US005744334A

United States Patent [19]
Dobres et al.

[11] Patent Number: 5,744,334
[45] Date of Patent: Apr. 28, 1998

[54] PLANT PROMOTER USEFUL FOR DIRECTING THE EXPRESSION OF FOREIGN PROTEINS TO THE PLANT EPIDERMIS

[75] Inventors: Michael S. Dobres, Philadelphia; Sevnur Mandaci, Ardsley, both of Pa.

[73] Assignee: Drexel University, Philadelphia, Pa.

[21] Appl. No.: 459,415

[22] Filed: Jun. 2, 1995

Related U.S. Application Data

[62] Division of Ser. No. 299,953, Sep. 2, 1994.
[51] Int. Cl.$^6$ .............................. A01H 5/00; C12N 5/04; C12N 15/82
[52] U.S. Cl. .................. 435/172.3; 435/69.1; 435/70.1; 435/320.1; 435/410; 435/419; 536/24.1; 800/205
[58] Field of Search .......................... 800/205; 435/69.1, 435/172.3, 240.4, 320.1, 70.1, 410, 419; 536/24.1

[56] References Cited

U.S. PATENT DOCUMENTS

| | | | |
|---|---|---|---|
| 4,672,035 | 6/1987 | Davidonis et al. | 435/240.5 |
| 5,110,732 | 5/1992 | Benfey | 435/172.3 |
| 5,164,316 | 11/1992 | McPherson et al. | 435/240.4 |
| 5,196,525 | 3/1993 | McPherson et al. | 536/24.1 |
| 5,322,938 | 6/1994 | McPherson et al. | 536/24.1 |
| 5,352,605 | 10/1994 | Fraley et al. | 435/240.4 |

FOREIGN PATENT DOCUMENTS

| | | |
|---|---|---|
| 2 187 462 | 9/1987 | United Kingdom. |
| WO 92/00371 | 1/1992 | WIPO. |
| WO 92/13957 | 8/1992 | WIPO. |

OTHER PUBLICATIONS

J.I. Medford, Vegetative Apical Meristems *Plant Cell* 1992, 4, 1029–1039.

Pak et al. Analysis of A Developmentally Regualted Putative Vegetative Lectin Gene in Pisum sativum L. Supplement to *Plant Physiology* 1992 99:17.

Dobres et al. An RNA Marker for Epidermal Differentiation in Pisum sativum Abstracts of Mid–Atlantic Plant Moleculor Biology Society 10th Annual Meeting Jul. 1993.

Vaeck et al., Transgenic plants protected from insect attack *Nature* 1987, 328, 33–37.

Broglie et al., Transgenic Plants with Enhanced Resistance to the Fungal Pathogen Rhizoctonia solani *Science* 1991, 254, 1194–1197.

Maiti et al., Transcripts for a lectin–like gene accumulate in teh epidermis but not the protodermis of the pea shoot apex *Planta* 1993, 190, 241–246.

Sterk et al., Cell–Specific Expression of the Carrot EP2 Lipid Transfer Protein Gene *Plant Cell* 1991, 3, 907–921.

Clark et al., Epidermis–Specific Gene Expression in Pachyphytum *Plant Cell* 1992, 4, 1189–1198.

Schmelzer et al., In Situ Localization of light–induced chalcone synthase mRNA, chalcone synthase, and flavonoid end products in epidermal cells of parsley leaves *Proc. Natl. Acad. Sci. USA* 1988, 85, 2989–2993.

Schmelzer et al., Temporal and Spatial Patterns of Gene Expression around Sites of Attempted Fungal Infection in Parsley Leaves *Plant Cell* 1989, 1, 993–1001.

Goodrich et al., A Common Gene Regulates Pigmentation Pattern in Diverse Plant Species *Cell* 1992, 68, 955–964.

Wyatt et al., Patterns of Soybean Proline–Rich Protein Gene Expression *Plant Cell* 1992, 4, 99–110.

Jefferson et al., GUS fusions: β–glucuronidase as a sensitive and versatile gene fusion marker in higher plants *EMBO J.* 1987, 6, 3901–3907.

Broglie et al., Light–Regulated Expression of A Pea Ribuloase–1,5–Bisphosphate Carboxylase Small Subunit Gene in Transformed Plant Cells *Science* 1984, 224, 838–845.

Atanassova et al., A 126 bp fragment of a plant histone gene promoter confers preferential expression in meristems of transgenic arabidopsis *Plant J.* 1992, 2, 291–300.

Guerrero et al., Promoter sequences from a maize pollen–specific gene direct tissue–specific transcription in tobacco *Mol. Gen. Genet.* 1990, 224, 161–168.

Stalberg et al., Deletion analysis of a 2S seed storage protein promoter of Brassica napus in transgenic tobacco *Plant Mol. Biol.* 1993, 23, 671–683.

Suzuki et al., Deletion analysis and localization of SbPRP1, a soybean cell wall protein gene, in roots of transgenic tobacco and cowpea *Plant Mol. Biol* 1993, 21, 109–119.

Bogusz et al., Nonlegume Hemoglobin Genes Retain Organ– Specific Expression in Heterologous Transgenic Plants *Plants Cell* 1990, 2, 633–641.

Koes et al., Chalcone Synthase Promoters in Petunia are Active in Pigmented and Unpigmented Cell Types *Plant Cell* 1990, 2, 379–392.

Liang et al., Developmental and environmental regulation of a phenylalanine ammonia–lyase–β–glucuronidase gene fusion in transgenic tobacco plants *Proc. Natl. Acad. Sci. USA* 1989, 86, 9284–9288.

(List continued on next page.)

*Primary Examiner*—Elizabeth McElwain
*Attorney, Agent, or Firm*—Woodcock Washburn Kurtz Mackiewicz & Norris LLP

[57] ABSTRACT

The present invention is directed to a Blec plant promoter sequence of SEQUENCE ID NO: 1. A method of transforming plants with a Blec promoter-gene construct is also within the scope of the present invention. The present invention is also directed to cells comprising a Blec promoter-gene construct, plasmids and vectors comprising a Blec promoter-gene construct and the constructs per se comprising a Blec promoter and a gene. A plant extract comprising all or part of the Blec promoter sequence and a gene under control of said promoter and a method of transcribing nucleic acids comprising an extract having all or part of the Blec promoter sequence and a gene under control of said promoter are also within the scope of the present invention.

4 Claims, 12 Drawing Sheets

OTHER PUBLICATIONS

*Plant Molecular Biology: A Practical Approach*, Ed. Shaw, C.H., IRL Press Limited, Oxford, England, 1988, pp. 131–160.

Mandaci and Dobres, Sequence of a Vegetative Homolog of the Pea Seed Lectin Gene *Plant Physiol.* 1993, 103, 663–664.

Arias et al., Dissection of the Functional Architecture of a Plant Defense Gene Promoter Using a homologous in Vitro Transcription Initiation System *Plant Cell* 1993, 5, 485–496.

W.F. Thompson, et al., Phytochrome control of RNA leveles in developing pea and mung–bean leaves *Planta* 1983, 158, 487–500.

J.H. Pak, et al., Predicted sequence and structure of a vegetative lectin in *Pisum sativum Plant. Mol. Biol.* 1992, 18, 857–863.

Valles M. Regeneration from *Rosa callus Acta Horticulturae* 1987 212:691–696.

Bevan, M. W., Binary Agrobacterium vectors for plant transformation *Nucleic Acids Res.* 1984, 12, 8711–8721.

Bingham, E.T., Registration of Alfalfa Hybrid Regen–Sy Germplasm for Tissue Culture and Transformation Research *Crop Sci.* 1991, 31, 1098.

Napoli et al., Introduction of a Chirmeric Chalcone Synthase Gene into Petunia Results in Reversible Co–Suppression of Homologous Genes in trans *Plant Cell* 1990, 2, 279–289.

Bevan et al., Structure and transcription of the nopaline synthase gene region of T–DNA *Nucleic Acid Res.* 1983, 11, 369–385.

J.A. Fleming, et al., The Patterns of Gene Expression in the Tomato Shoot Apical Meristem *Plant Cell* 1993, 5, 297–309.

S. Gnatt and J.L. Key, Molecular cloning of a pea H1 histone cDNA *Eur. J. Biochem.* 1987, 166, 119–125.

Higgins, T.J.V., et al., The Biosynthesis and Primary Structure of Pea Seed Lectin *J. Biol. Chem.* 1983, 258, 9544–9549.

Dobres et al. Molecular Analysis of a Shoot Apex Protein in *Pisum sativum Supplement to Plant Physiology* May 1993 102:11.

Dobres et al. A Developmentally Regulated Bud Specific Transcript in Pea Has Sequence Similarity to Seed Lectins *Plant Physiol* 1989 89:833–838.

Lamb et al. Emerging Strategies for Enhancing Crop Resistance to Microbial Pathogens *Bio/Technology* 1992 10:1436–1445.

```
39kd                                                                LSFNFPKITP
                                                                    ||||||||||
BLEC1  1 MG1      yrtkeLLSLLvsimfvsla   TN iealSFnfpkitpgntaitLQGnAKIL
LOTTE  1                                    vSF xytefkdagsLILQGDAKIw
PHAVU  1 MA      ssnLLSL   aLfLVLLT hANSAsqtfFS   fdrfnetNLILQGDA sV
SOYBN  1 MA tSK lktqnvvvsLSLtitLVLVLLTSkANSAetvsFSwNKFvpkQpNmILQGDA iV
CDNA   1 MA iSKkssIFlpIFtfFltmflmVvnKVsSSThETnalhFmFNqFSKDQkdLILQGDA TT
PEA    1 MAslqtqmisFyaiFLsIllttilffKV nST ET  tsFlitkFSpDQqnLIFQGDgyTT
```

*FIG. 11*

PLANT PROMOTER USEFUL FOR DIRECTING THE EXPRESSION OF FOREIGN PROTEINS TO THE PLANT EPIDERMIS

This is a division of application Ser. No. 08/299,953, filed Sep. 2, 1994.

REFERENCE TO GOVERNMENT GRANTS

This work was supported in part by a research grant from the United States Department of Agriculture, grant number 89-37262-4793. The United States Government may have certain rights in this invention.

BACKGROUND OF THE INVENTION

Plant shoot growth occurs mainly from the continual activity of the apical meristem. The biochemical and cytological events associated with apical growth are of paramount importance in understanding plant development. Numerous studies have utilized histological, surgical and genetic approaches to analyze the properties of the apical meristem, for example, J. I. Medford, *Plant Cell* 1992, 4, 1029–1039. The apical meristem is commonly described in terms of three generative tissue layers, S. Satina, et al., *Am. J. Bot.* 1940, 27, 895–905. The outer layer, the L1 layer, divides mostly in plane anticlinical to the surface of the apical meristem and gives rise to the shoot epidermis. Cells of L2 layer divide mainly in an anticlinical plane, but divide periclinically during primordia formation. Cells of the L3 layer divide in all planes and give rise to the central core of the plant.

Although the fate of cells produced within the apical meristem is clear, much remains to be learned about the regulatory events that occur during cell differentiation. For example, what processes define the differentiation of a cell from the L1, L2, or L3 layers as it emerges from the apical meristem and slowly develops into a fully differentiated shoot cell. In the case of the L1 layer, it is known that mature epidermal cells arise by successive anticlinical divisions from the protodermis of the apical meristem, but are there any specific molecular or cytological changes involved in the differentiation of cells arising from the apical meristem? As judged by light microscopy there is no clear visible demarcation between proto- and epidermal cells in pea, B. F. Thomson and P. M. Miller, *Am. J. Bot.* 1962, 49, 303–310. In fact, in pea, epidermal cells remain undifferentiated and indistinguishable from the internal tissue as far as five nodes from the apical meristem in 8 day old seedlings, Thomson and Miller, supra.

The plant epidermis represents the primary barrier and interactive surface with the environment (Esau, K, *Anatomy of Seed Plants*. John Wiley and Sons, Inc., New York, 1960). Molecules and structures within the epidermis are believed to play roles in defense from microbial or animal attack, attracting beneficial insects by the synthesis of pigments or volatile chemicals, mechanical support, and prevention of water loss. Since plants and plant pests have co-evolved over millions of years, a plant's natural defenses are often inadequate to protect it from microbial or animal attack. The introduction of foreign genes, cloned from plant, animal, and/or microbial sources, by genetic engineering, represents a strategy with which to enhance the defense properties of a plant. Examples of this strategy include transgenic tobacco plants protected from insect attack using the *Bacillus thuringiensis* endotoxin expressed under the control of $^{35}$S CaMV promoter (Vaeck et al., *Nature* 1987, 328, 33–37), and tobacco plants protected against fungal attack using a bean chitinase expressed under the control of the CaMV promoter (Broglie et al., *Science* 1991, 254, 1194–1197.

For optimal efficiency, the genetically engineered defense molecule should be highly expressed in the plant tissue first encountered by the pest which in most cases is the outer epidermis.

Maiti et al. (Maiti et al., *Planta* 1993, 190, 241–246) reported the characterization of mRNA sequences encoding a lectin-like protein, and corresponding cDNAs that accumulate in the shoot-apex epidermis of the garden pea (*Pisum sativum*). Others (Sterk et al., *Plant Cell* 1991, 3, 907–921) have reported the characterization of mRNA sequences encoding a lipid transfer protein gene that is highly expressed in epidermal cells of carrot shoot-apices.

Clark et al. (Clark et al., *Plant Cell* 1992, 4, 1189–1198) reported the characterization of mRNA sequences of lipid transfer protein genes expressed in the epidermis of Pachyphytum.

Other examples of mRNA specific to the epidermis include reports by Schmelzer et al. (Schmelzer et al., *Proc. Natl. Acad. Sci. USA* 1988, 85, 2989–2993; Schmelzer et al., *Plant Cell* 1989, 1, 993–1001) who identified mRNAs encoding chalcone synthase (CHS) and phenyl-alanine ammonia lyase (PAL) gene families that accumulate in epidermal cells in response to chemical induction. In the absence of induction PAL and CHS mRNAs are expressed in parenchymotous mesophyll tissue as well.

Goodrich et al. (Goodrich et al., *Cell* 1992, 68, 955–964) reported that mRNAs encoding enzymes involved in anthocyanin biosynthesis in snapdragon flowers are expressed in specialized epidermal cells for limited periods during flower bud development. Wyatt et al. (Wyatt et al., *Plant Cell* 1992, 4, 99–110) reported that mRNAs encoding the soybean proline-rich cell wall proteins SbPRP1, SbPRP2, and SbPRP2 accumulate at certain developmental stages in the epidermis but are expressed at different times in the vascular tissue as well.

To demonstrate which portion of a gene is required to direct the pattern of tissue specific expression described above, it is necessary to isolate the putative regulatory region of a gene and test its ability to direct the expression of a reporter gene in transgenic plants. This may involve, for example, placing the promoter (5' upstream region) of a gene in combination with the coding region of a reporter gene, for example the bacterial gene β-glucuronidase. Jefferson et al., *EMBO J.* 1987, 6, 3901–3907. β-Glucuronidase activity can be readily assayed in situ using the chromogenic substrate 5-bromo-4-chloro-3-indolyl-β-D-glucuronic acid.

Promoters shown to direct tissue specific expression include those active in mesophyll and palisade of leaves (Broglie et al., *Science* 1984, 234, 838–845), dividing shoot and root tissues meristems (Atanassova et al., *Plant J.* 1992, 2, 291–300), pollen, (Guerrero et al., *Mol. Gen. Genet.* 1990, 224, 161–168), seed endosperm, (Stalberg et al., *Plant Mol. Biol.* 1993, 23, 671–683), root epidermis (Suzuki et al., *Plant Mol. Biol* 1993, 21, 109–119) and root meristems, vascular tissue and nodules (Bogusz et al., *Plant Cell* 1990, 2, 633–641). The literature contains relatively few reports of promoters that are expressed in the epidermis, this includes promoters active in the epidermal cells of flowers (Koes et al., *Plant Cell* 1990, 2, 379–392) and those are expressed in the epidermis in response to wounding (Liang et al., *Proc. Natl. Acad. Sci. USA* 1989, 86, 9284–9288). There are no known reports of promoters capable of directing expression to the epidermis of the growing shoot tip.

SUMMARY OF THE INVENTION

The present invention is directed to a Blec plant promoter sequence of SEQUENCE ID NO: 1. A method of transforming plants with a Blec promoter-gene construct is also an embodiment of the present invention. The present invention is also directed to cells comprising a Blec promoter-gene construct, plasmids and vectors comprising a Blec promoter-gene construct and the constructs comprising a Blec promoter and a gene, per se. A plant extract comprising all or part of the Blec promoter sequence and a gene under control of said promoter and a method of transcribing nucleic acids comprising an extract having all or part of the Blec promoter sequence and a gene under control of said promoter are also within the scope of the present invention.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1A, apical meristem; FIG. 1B, a single floral primordium with undifferentiated floral dome flanked by sepal primordia; FIG. 1C, a floral bud showing sepal, petal, anther, and ovary primordia; FIG. 1D, unopened flower bud post-pollination showing accumulation of Blec RNA on outer epidermis of ovary.

FIG. 2A and FIG. 2C, thin sections of ovary. FIG. 2B, autoradiogram of A after hybridization with radiolabelled Blec antisense RNA; FIG. 2D, autoradiogram of FIG. 2C after hybridization with radiolabelled histone H1 antisense RNA.

FIG. 7A is a longitudinal section through alfalfa shoot apex (4x); in FIG. 7B, the magnification of epidermis shown in FIG. 7A is 20x; FIG. 7C is a longitudinal section through a torpedo stage somatic embryo (10x).

FIG. 10A: Coomassie blue stained gel, lane 1: 150 mM eluate; lane 2: 10 mM wash, lane 3: 30–80% ammonium sulfate precipitate, lane 4: total bud extract, lane 5: total seed extract, lane 6: molecular weight markers. FIG. 10B: Western blot of an identical gel probed with anti-pea seed lectin. Lanes 1–5: as in FIG. 10A. FIG. 10C: ponceau S stain of FIG. 10B, before antibody probing.

FIG. 11 is a comparison of N terminal amino acid sequences of protein purified from total extracts of pea shoot apices compared to the deduced amino acid sequence of Blec and other legume lectins: PEA, pea seed lectin sequence.

DETAILED DESCRIPTION OF THE INVENTION

Figure 1:
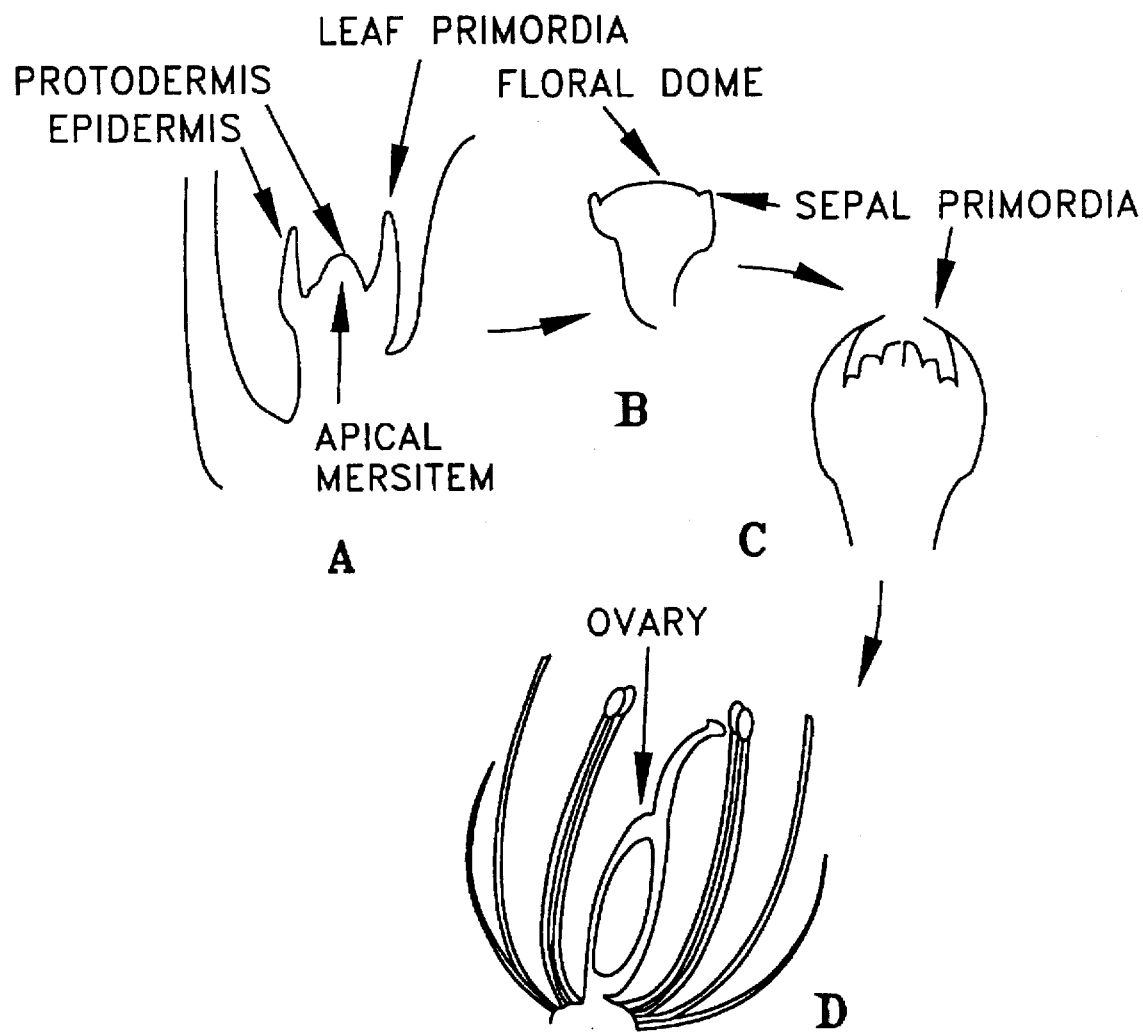
FIGS. 1A–D is a summary of tissue specific RNA accumulation during vegetative and floral development. Thick black lines represent tissue specific expression in the epidermis. Thin black lines represent protodermal cells that do not accumulate detectable levels of Blec transcripts. Blec RNA is undetectable in the protodermis of vegetative and floral meristems. Blec first accumulates to detectable levels on the abaxial or out surface of developing primordia.

The present invention is directed to nucleic acid sequences for a plant promoter of SEQUENCE ID NO: 1. The Blec promoter is useful in targeting genes, including foreign genes, to the epidermis of plants. Accordingly, the invention is directed to epidermal specific expression of genes and/or sequences. The promoter is named Blec, an acronym for bud lectin, a vegetative sequence homologue of the pea seed lectin (PSL), Mandaci and Dobres, *Plant Physiol.* 1993, 103, 663–664. Four cDNAs exist for the coding region of Blec. Pak et al., *Plant Molecular Biology* 1992, 18:857–863. The promoter set forth by the present invention is located 5' of the coding region in Blec4. The coding region of the Blec protein shares a high degree of sequence identity with Blec1, Blec2, and Blec3. Similarly, the promoter sequences of the Blec genes are expected to share extensive sequence similarity.

The Blec promoter is 3881 nucleotides in length. All or part of the Blec promoter may be used to specifically direct a sequence or gene to the epidermis of plants. All or part of the Blec promoter may be fused with a protein product of a sequence or gene and expressed in the plant epidermis. A portion, a part, a fragment, or the like, refers to one or more groups of nucleic acids within the Blec promoter which control the epidermal expression of genes which are ligated to the promoter. All or part of the Blec promoter sequence may be used to direct other sequences to plant epidermal cells. All or part and nucleic acid sequences which are substantially similar to the nucleic acid sequence of the Blec promoter, for purposes of the present invention, relates to a nucleic acid sequence which is preferably 25%, preferably 50%, more preferably 75%, and most preferably 100% identical to the Blec promoter. The portion of the Blec promoter sequence may be in a single consecutive arrangement, or more than one arrangement of consecutive nucleic acids. In addition, the present invention includes sequences which are substantially similar to the sequence of SEQUENCE ID NOS: 1 or 2, or portions thereof. Substantially similar, for purposes of the present invention is a sequence which is preferably 25%, preferably 50%, more preferably 75%, and most preferably 100% identical to SEQUENCE ID NO: 1. All or part of SEQUENCE ID NOS: 1 or 2 may be used to specifically direct a sequence or gene to the epidermis.

Blec RNA is highly expressed within specific phases of meristematic epidermal cell development, it accumulates specifically in meristematic epidermal cells of vegetative and floral organs, but is undetectable in protodermal cells that bind vegetative or floral meristems. During early vegetative and floral primordia development, Blec accumulates mainly on the abaxial epidermis and is undetectable on the adaxial or inner surface of such organs. The accumulation of Blec thereby not only defines the epidermis, but also specific stages and positions of epidermal tissue during organ development. These observations are discussed with a view to further defining the regulatory events involved in epidermal differentiation.

The Blec promoter is useful in ligating or fusing to the 5' end of another sequence or gene, thereby producing a Blec promoter-gene construct, to be directed to the epidermal cells of a plant. Epidermal cells which express Blec include and are not limited to epidermal cells of the shoot, leaves, flowers, stem, fruit, vegetative, and reproductive organs. In accordance with the present invention, epidermal cells include and are not limited to the outer layer of cells, the sub-epidermis, which is at least one layer of cells immediately below the epidermis, and the L1 layer of the shoot apex, of each of the plant parts identified in the foregoing sentence. Species variability may exist in plants which express Blec, therefore, those layers which are found to express Blec and Blec-gene constructs or which are cytologically similar to the epidermis are included in the definition of epidermis of the present invention. Thus, the Blec promoter is ligated in frame upstream of a sequence to be epidermally expressed.

Downstream or 3' of the sequence to be expressed may be suitable transcription termination signals, including a polyadenylation signal or other sequences found helpful in the processing of the 3' mRNA terminus. A marker sequence or gene may also be ligated 3' of the Blec promoter. The marker sequence may provide a means of easily identify the epidermal cells expressing the sequences under control of the Blec promoter.

In accordance with the present invention, constructs include and are not limited to nucleic acid sequences which are not limited to DNA, such as cDNA and genomic DNA; RNA, such as mRNA and tRNA; suitable nucleic acid sequences such as the sequences set forth in SEQUENCE ID NOS: 1 or 2, and conservative alterations in nucleic acid sequences including additions, deletions, mutations, and homologues. The sequences within the scope of the present invention include antisense sequences which may alter plant characteristics, including those identified above. Antisense sequences may prevent the translation of sequences in the epidermis which are detrimental to the plant. Inhibiting of expression of certain sequences, such as those responsible for the characteristics identified herein, may be achieved with antisense sequences.

In accordance with the invention, the sequences employed in the invention may be exogenous and heterologous sequences. Exogenous and heterologous, as used herein, denote a nucleic acid sequence which is not obtained from and would not normally form a part of the genetic make-up of the plant or the cell to be transformed, in its untransformed state. Plants comprising exogenous or heterologous nucleic acid sequences of Blec, such as and not limited to the nucleic acid sequence of SEQUENCE ID NUMBER: 1, are within the scope of the invention. The sequence or gene to be epidermally expressed may be foreign such that a chimeric sequence is delivered to the plant. Foreign genes and sequences, for purposes of the present invention, are those which are not naturally occurring in the plant into which they are delivered. A chimeric construct results from a foreign sequence or gene ligated to the Blec promoter, optionally together with other sequences.

Also amino acid, peptide, polypeptide, and protein sequences of the Blec-gene construct are within the scope of the present invention. Conservative alterations in the amino acid sequences including additions, deletions, mutations and homologues are also included within the scope of the present invention.

The present invention is also directed to a method of transforming plants comprising making available at least one plant cell, preparing a construct of a Blec promoter together with a gene thereby forming a promoter-gene construct, transforming the plant cell with the promoter-gene construct thereby preparing a transformed plant and allowing expression of the sequence encoding the Blec promoter-gene construct. The plants maybe prepared in culture. The promoter-gene construct may be incorporated into the plant sequence or may be part of a plasmid or vector which then transforms the plant. Plasmids and/or vectors which comprise a Blec promoter-gene construct and a cell, including cells in culture, which comprises a Blec promoter-gene construct are also within the scope of the present invention. Methods of delivering the sequences to the plant include and are not limited to electroporation, microprojectile, microinjection.

Expression vectors, host cells and cell cultures suitable for use in the invention are chosen from expression systems capable of synthesizing Blec promoter-gene constructs.

Nucleic acids coding for the Blec promoter and constructs comprising the Blec promoter may be expressed in plant cell culture or in fungal cells for the production of recombinant proteins. Plant cells include cell or cell culture derived from any seed or non-seed plant including and not limited to the plants set forth in accordance with the present invention.

Fungal cells include and are not limited to members of Ascomycete, including Saccharomyces, such as *cerviseae* and *carlsbergensis*, Schizosaccharomyces such as *pombe*, Aspergillus such as *nidulanst*, Neurospora such as *crossa*; as well as Basidromycete, Oomycete, and *Fungi Imperfecti*.

As used herein, expression vectors refer to any type of vector that can be manipulated to contain a nucleic acid sequence coding for the Blec promoter and constructs, such as plasmid expression vectors and viral vectors. The selection of the expression vector is based on compatibility with the desired host cell such that expression of the nucleic acid coding for the Blec promoter and constructs results. In general, plasmid vectors contain replicon and control sequences derived from species compatible with the host cell. To facilitate selection of plasmids containing nucleic acid sequences of the invention, plasmid vectors may also contain a selectable marker such as a gene coding for antibiotic resistance. Suitable examples include, and are not limited to, the genes coding for ampicillin, tetracycline, chloramphenicol or kanamycin resistance.

Suitable expression vectors, enhancers, and other expression control elements are known in the art and may be found in *Plant Molecular Biology: A Practical Approach*, Ed. Shaw, C. H., IRL Press Limited, Oxford, England, 1988, pages 131–160 and Sambrook et al., *Molecular Cloning: A Laboratory Manual*, second edition, Cold Spring Harbor Laboratory Press, Cold Spring Harbor, N.Y. (1989), incorporated herein by reference in their entirety.

The particulars for the construction of expression systems suitable for desired hosts are known to those in the art. For recombinant production of the protein, the DNA encoding it is suitably ligated into the expression system of choice and the system is then transformed into the compatible host cell which is then cultured and maintained under conditions wherein expression of the foreign gene takes place. The peptide of this invention may then be recovered from the culture, either by lysing the cells or from the culture medium as appropriate and known to those in the art.

The expression vector including the nucleic acid sequence coding for Blec promoter and constructs comprise transcription and translation control elements. For example, in an upstream position may be a translation initiation signal comprising a ribosome binding site and an initiation codon, and in a downstream position may be a transcription termination signal. The transcription and translation control elements may be ligated in any functional combination or order. The transcription and translation control elements used in any particular embodiment of the invention will be chosen with reference to the type of cell into which the expression vector will be introduced, so that an expression system is created. Transformed host cells containing a DNA sequence coding for the Blec promoter and constructs may then be grown in an appropriate medium for the host.

The present invention is also directed to a plant extract comprising all or part of the Blec promoter sequence and a gene under control of said promoter. The extract is cell-free and may be synthetic or natural. The extract may also include cell parts such as and not limited to nuclei or parts thereof, polymerases, ribosomes, amino acids, nucleotides, various salts, buffers, and inorganic or organic substances deemed to be helpful in the use of the extract.

A method of transcribing nucleic acids comprising an extract having all or part of the Blec promoter sequence and a gene under control of said promoter is also within the scope of the present invention. Conditions for performing the method are known to those of skill in the art, Arias et al., *Plant Cell* 1993, 5, 485–496, incorporated herein by reference in its entirety. The extract may also translate the RNA, which was transcribed, into protein.

The present invention includes the transformation of plants with genes which provide advantageous characteristics, including and not limited to altering (increasing or decreasing) insect, viral, and/or disease resistance; result in increased fragrance, petal pigmentation, color brilliance, growth rate, and longer flower life. Foreign genes responsible for characteristics, including those identified above, include and are not limited to resistance to microbial pathogens, chitinases, glucanases, and other enzymes capable of hydrolyzing fungal cell walls, ribosome-inactivating proteins such as enzymes and proteins induced by wounding or microbial attack, including those induced by salicylic acid, jasmonic acid, 2, 6, 1, chloroisonicotinic acid; lysozymes from non-plant sources including and not limited to phage T4 lysozyme, mammalian lysozymes; phenylammonia lyase or other enzymes of the phenylpropanoid pathway which catalyze the formation of a wide range of natural products based on the phenylpropane skeleton, such as lignin, phytoalexins, pterocarpons, furanocoumarins, and isoflavone 2-hydroxylase; enzymes involved in lignin polymerization such as anionic peroxidases; enzymes involved in the biosynthesis of alkaloids including benzophenanthridine, alkaloids and indole alkaloids; enzymes in terpene biosynthesis, such as monoterpenes and sesquiterpenes; *Bacillus thuringiensis* endotoxins, glucanases, lectins including phytohemagglutinin, snowdrop lectin, wheatgerm agglutinin, as well as other proteins, including arcelin, α-amylase inhibitor, and the Blec protein, which share sequence homology with lectins; protease inhibitors such as cowpea trypsin inhibitor; cell wall proteins including glycine hydroxyproline rich proteins such as exlensins; enzymes involved in cellulose biosynthesis, plant cuticle biosynthesis including lipid biosynthesis and transport; RNases and ribozymes; and the like.

Transformation in accordance with the present invention may include resistance genes cloned by differential expression with respect to plant genotype, tissue-specificity or physiological conditions, transposon tagging; map based cloning; biochemical characterization of binding sites, for race specific elicitors, and shotgun cloning by function. Transformed plants having such characteristics are also within the scope of the present invention.

Methods of delivering the sequences into plants are known in the art, including and not limited to Ti-plasmid vectors, in vitro protoplast transformation, plant virus-mediated transformation, and liposome-mediated transformation.

Blec-gene constructs may be useful in home gardening such as in ornamental plants and flowers, shrubs, lawn grass, as well as cut flowers, including and not limited to Angiosperms, Bryophytes such as Hepaticae (liverworts) and Musci (mosses); Pteridophytes such as ferns, horsetails, and lycopods; Gymnosperms such as conifers, cycads, Ginkgo, and Gnetales; and Algae including Chlorophyceae, Phaeophpyceae, Rhodophyceae, Myxophyceae, Xanthophyceae, Bacillariophyceae (Diatoms), and Euglenophyceae. The plants within the scope of the present invention include and are not limited to the Families Rosaceae including roses, Ericaceae including rhododendrons and azaleas, Euphorbiaceai including poinsettias and croton, Caryophyllaceae including carnations, Solanaceae including petunias, Gesneriaceae including african violets, Balsaminaceae including impatiens, Orchidaceae including orchids, Iridaceae including Gladiolas, Irises, Freesia, and Crocus, Compositae including marigolds, Geraniaceae including geraniums, Lilaceae including dracaena, Moraceae including ficus, Araceae including philodendron, and the like. In addition, flowering plants including and not limited to the Families Leguminosae including pea, alfalfa, and soybean; Gramineae including rice, corn, wheat; solanaceae including tobacco, and the like; the Family Umbelliferae, particularly of the genera Daucus (particularly the species *carota*, carrot) and Apium (particularly the species *graveolens dulce*, celery) and the like; the Family Solanacea, particularly of the genus Lycopersicon, particularly the species *esculentum* (tomato) and the genus Solanum, particularly the species *tuberosum* (potato) and *melongena* (eggplant), and the like, and the genus Capsicum, particularly the species *annum* (pepper) and the like; and the Family Leguminosae, particularly the genus Glycine, particularly the species *max* (soybean) and the like; and the Family Cruciferae, particularly of the genus Brassica, particularly the species *campestris* (turnip), *oleracea* cv Tastie (cabbage), *oleracea* cv Snowball Y (cauliflower) and *oleracea* cv Emperor (broccoli), and the genus Arabidopsis, especially the species *thaliana*, and the like; the Family Compositae, particularly the genus Lactuca, and the species Sativa (lettuce), and the like.

In accordance with the present invention, the present plants included within the scope of the present invention are all species of higher and lower plants of the Plant Kingdom. Mature plants, seedlings, and seeds are included in the scope of the invention. The Blec promoter-gene constructs are useful in plants, plant parts, seeds, and plant culture. A mature plant includes a plant at any stage in development beyond the seedling. A seedling is a very young, immature plant in the early stages of development. Annuals, perennials, monocotyledons and dicotyledons may also be transformed with the Blec promoter and Blec-gene constructs.

The present invention may also be helpful in isolating DNA binding proteins involved in regulation of the Blec promoter as well as other promoters in the epidermis.

EXAMPLES

Initial Isolation of a Blec4 Genomic Clone

RNA was isolated and probed according to the methods of W. F. Thompson, et al., *Planta* 1983, 158, 487–500, incorporated herein by reference in its entirety. Genomic Southern blots were performed as described in Maniatis et al., *Molecular Cloning. A Laboratory Manual.* Cold Spring Harbour Laboratory Press, New York, 1982, incorporated herein by reference in its entirety. DNA probes were labelled with $^{32}$P using the Amersham Multiprime™ kit as per the manufacturer's instructions. The probe used for hybridization was a BamHI-SacI 900 bp full length cDNA insert from pBlec1, isolated by J. H. Pak, et al., *Plant. Mol. Biol.* 1992, 18, 857–863, incorporated herein by reference its entirety.

Figure 3:
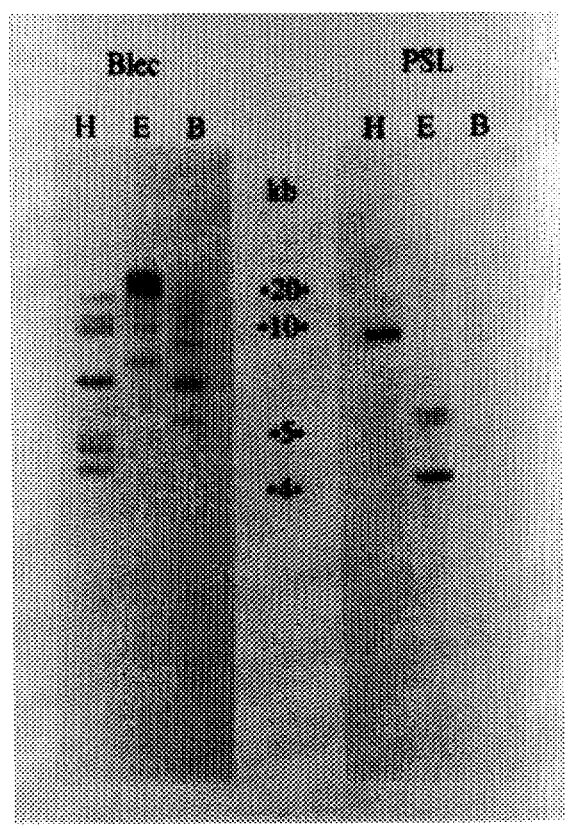
FIG. 3, a comparative Southern analysis between Blec and the pea seed lectin (PSL) gene, reveals multiple genomic copies for Blec and 1–2 for PSL. The same blot was used for both Blec and PSL probings. H, HindIII, E, EcoRI; B, BamHI.
Figure 4:
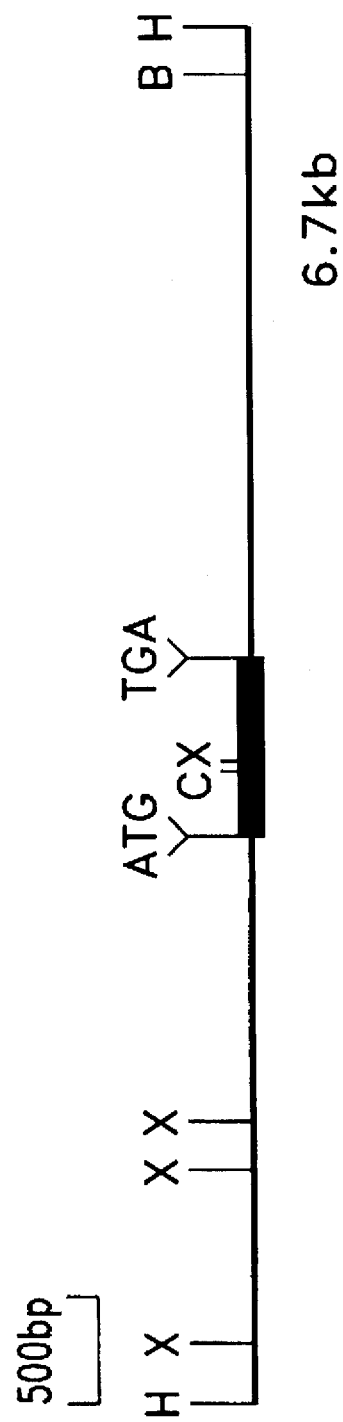
FIG. 4 is a restriction enzyme map of the Blec4 genomic clone. H, HindIII; X, XbaI; C, ClaI, B, BamHI. Bold bar, position of Blec4 coding region.

Southern analysis of HindIII digests revealed 8 genomic fragments ranging from 4–20 kb. The presence of multiple genomic copies of the Blec gene, is consistent with the results of CDNA analysis: a 6.7 kb HindIII genomic fragment was isolated from the λ phage λ29 which was isolated from a λL47.1 genomic library of *Pisum sativum* var. Alaska (FIG. 3). This contrasts with the pea seed lectin (PSL) gene which is represented by a single genomic fragment, and therefore appears to be encoded by a single copy gene per haploid genome (FIG. 3). Restriction fragment length polymorphism analysis reveals that the two sets of genes, Blec and PSL, are located within 10 CM of each other on chromosome seven. Such genetic linkage is consistent with the notion that the two sets of genes arose from a common ancestral gene by a process of duplication.

The 6.7 Kb fragment was ligated into the HindIII site of the *E. coli* vector pKSM13+ (Stratagene™, LaJolla, Calif.). Sequence analysis revealed p29H6 contains a single coding region identical to the Blec4 cDNA clone (S. Mandaci and M. Dobres, *Plant Physiol.* 1993, 93, 663–664). This not only indicates its identity, but also indicates that it corresponds to an expressed member of the Blec gene family.

Expression of the Blec4 Genomic Clone in Transgenic Alfalfa

The 6.7 kb genomic fragment was cloned into the binary vector pBIN19, prepared according to the methods of Bevan, M. W., *Nucleic Acids Res.* 1984, 12, 8711–8721, incorporated herein by reference in its entirety, to create the vector pBIN6K, electroporated into *Agrobacterium tumefaciens*, strain LBA4404, and used to transform leaf segments of alfalfa var. RegenSY (Bingham, E. T., *Crop Sci.* 1991, 31, 1098, incorporated herein by reference in its entirety). Bevan et al. disclose the production of vector molecules chimeric nopaline synthase-neomycin phosphotransferase genes, utilize a restriction fragment from Tn5 containing the coding region of neomycin phosphotransferase to create pUC9-nopneoΔ.

This molecule provides a convenient skeleton upon which left and right borders of T-DNA from pTiT37 could be assembled. The HindIII restriction fragment containing the right border also contained an intact nopaline synthase gene, which is a useful screenable marker as nopaline is not found in untransformed plant tissues. The T-DNA array of left and right borders and selectable marker was ligated into a derivative of the wide host range plasmid pRK252 that contained a type III aminoglycoside phosphotransferase for selection in Agrobacterium. The prototype binary vector Bin 6 (15 kb) was obtained, which contains restriction sites with T-DNA for SalI and EcoRI, an efficient selectable marker gene and a screenable gene for identifying putative transformants. The prototype was modified by the deletion of unwanted sequences. The nopaline synthase gene was removed by a partial SStII digestion and religation, and excess Ti plasmid sequences (approximately 1.5 kb) flanking the left and right border repeats were removed by partial Bal31 exonuclease treatment. The truncated T region thus obtained was cloned into pRK252 derivative that has suffered a 2.5 kb deletion during the insertion of the kanamycin resistance gene from Streptococcus. Finally, to aid insertion of sequences into the T-region of the vector, a 440 bp HaeII fragment from ml3mpl19, was inserted in place of a 1.6 kb EcoRI fragment 80 bp from the left border of T-DNA to provide unique sites for EcoRI, BamHI, HindIII, SStI, KpnI, SmaI, XbaI, and SalI within the vector DNA. Plasmids harboring inserts in this sequence can conveniently be identified on plates containing kanamycin IPTG and X-gal. Leaf segments were surface sterilized and co-cultivated for two days on Murashiga and Skoog Basal Salt media, MS, (GibcoBRL, Grand Island, N.Y.) with *Agrobacterium tumefaciens* LBA4404 containing either pBI121, prepared according to the methods of Jefferson, R. A., et al., *EMBO J.* 1987, 6, 3901–3907, incorporated herein by reference in its entirety, or pBIN6K. pB121 construction was made by ligating the coding region of GUS, EC3.2.1.31 (a DNA sequence encoding β-glucuronidase from *E. coli*, see Jefferson, supra.) linked to the 5' end of the nopaline synthase polyadenylation site, in the polylinker site of pBIN19. Bevan et al., *Nucleic Acid Res.* 1983, 11, 369–385, incorporated herein by reference in its entirety. This vector pBI101 contains unique restriction sites for HindIII, SalI, XbaI, BamHI and SmaI upstream of the AUG initiator codon of GUS, to which promoter DNA fragments can be conveniently ligated. The cauliflower mosaic virus (CaMV) 35S promoter was ligated into the HindIII and BamHI sites to create pBI121.

Explants were then washed with sterile water and transferred to Gamborg's B-5 (Gb5) plates containing 100 μg/ml Kanamycin and 500 μg/ml Carbenicillin. Somatic embryos were observed within 6 weeks, after which they were transferred to hormone free media (Gb5) to allow for further embryo growth. After a further 4 weeks embryos were transferred to ½× MS for rooting. After a further 4–8 weeks plants were transferred to soil.

Figure 5:
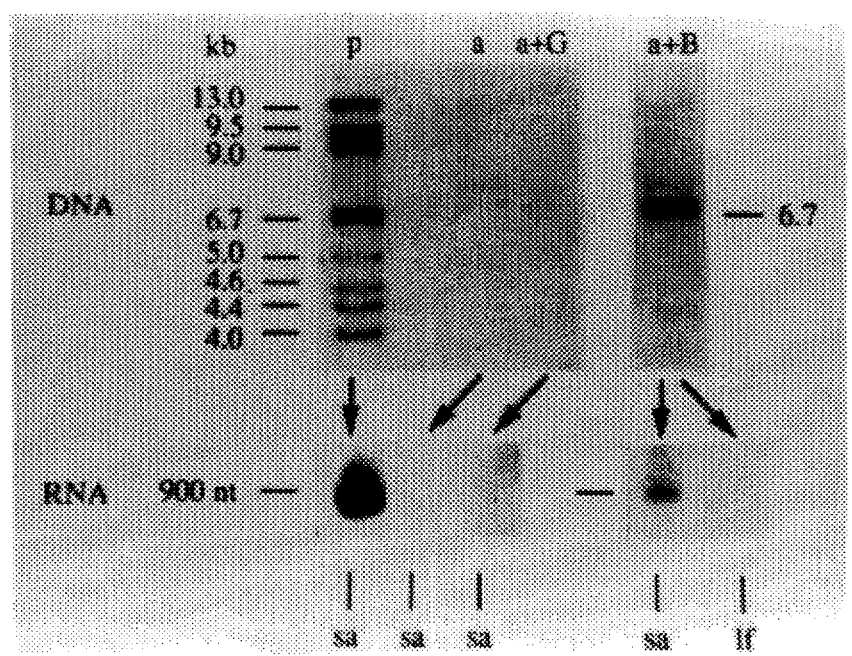
FIG. 5 exhibits a Southern and Northern blots of transgenic alfalfa probed with a full length Blec cDNA insert, p, pea genomic DNA; a, alfalfa var. RegenSY genomic DNA; a+G, alfalfa var. RegenSY transformed with pBI121; a+B, alfalfa var. RegenSY transformed with a Blec4 6.7 kb genomic fragment; sa, shoot apex; if, expanded leaf. The arrows indicate the source of the RNA used in the Northern blots.

Southern analysis of HindIII digests of the transformed alfalfa line revealed that the line contained at least one intact copy of the 6.7 kb HindIII insert (FIG. 5). Faint signals of approximately 7 kb are seen in lanes containing genomic DNA from untransformed alfalfa and alfalfa transformed with pBI121 containing a 35S-GUS-NOS construct (Jefferson, R. A., supra). The 7 kb fragment may represent cross hybridization to endogenous genomic DNA.

Northern analysis shown in FIG. 5 reveals that the transgenic alfalfa line expresses the Blec4 genomic clone in an apex-specific manner: its RNA accumulates in the shoot apex, but not in expanded leaves below the shoot apex. Negative controls using untransformed alfalfa and alfalfa transformed with pBI121 carrying a 35S-GUS-NOS construct show that at the hybridization stringency used (5× SSC, 30% formamide, 42° C.) it is possible to distinguish between Blec and endogenous alfalfa transcripts. Endogenous transcripts of a similar size are only seen at very low stringencies (5× SSC, 42° C.).

The intensity of the Blec4 signal in transgenic alfalfa (FIG. 5, lane a+b) is less than that of the total Blec signal seen in pea (FIG. 5, lane p). This difference may reflect the fact that Blec4 is but one member of a multi-gene family, the possible low intrinsic activity of the Blec4 promoter and co-suppression due to interaction of the Blec4 gene with endogenous alfalfa genes (Napoli et al., *Plant Cell* 1990, 2, 279–289).

Stage and Position Dependent Epidermal Expression

To learn more about how the expression of Blec correlates with the growth and development of the shoot apex, an extensive series of in situ hybridizations were carried out using Blec and several control probes. Maiti et al., *Planta* 1993, 190, 241–246, incorporated herein by reference in its entirety. The results of these studies are summarized in FIG. 1.

In situ hybridization was performed according to the methods of Maiti et al., supra. except that data presented in FIG. 2 were visualized by autoradiography by exposure to XAR5 X-ray film.

Histochemical localization was performed as follows. Plant material was fixed in 90% acetone for 1 hour, at room temperature and washed with 50 mM Sodium Phosphate, pH 7, for 2 hours. Plant material was then sectioned on a vibrotome to a thickness of 50 µM. Sections were then incubated in 100 mM sodium phosphate, 10 mM EDTA, 0.5 mM potassium ferricyanide, 0.5 mM potassium ferrocyanide and 1 mM 5-bromo-4-chloro-3-indolyl β-D-glucuronide for 3 hours and fixed in a solution containing 5% formaldehyde, 5% acetic acid and 20% ethanol for 10 minutes, washed with 50% ethanol for 2 minutes and finally washed with 95% ethanol before placing on slides and mounting with 80% glycerol. Sections were viewed with X10 and X40 objectives on a Nikon Photomat microscope and photographed using Ektachrome T160 film.

These studies revealed that Blec RNA is highly expressed in epidermal cells flanking the apical meristem but is undetectable in protodermal cells of the shoot apical meristem. The difference in transcript levels between the protodermis and the derived epidermis represents a clear regulatory transition within a single cell type. This represents the first indication of a gene-regulatory difference between the protodermis of the apical meristem and the flanking epidermal cells that arise from it. Blec RNA accumulation is distinct from other RNAs so far characterized in the shoot apex. Other RNAs accumulate at detectable levels in both protodermal and flanking epidermal cells; as in the case of carrot shoot apices, P. Sterk, et al., *Plant Cell* 1991, 3, 907–921, and three epidermal specific cDNAs from Pachyphytum, (A. M. Clark, et al., *Plant Cell* 1992, 4, 1189–1198). Although not restricted to the epidermis, other examples of transcripts whose expression is reduced within the apical meristem include napin and RbcS transcripts, which although present at high levels throughout the shoot apex, are greatly reduced within the vegetative apical meristem of tomato, J. A. Fleming, et al., *Plant Cell* 1993, 5, 297–309.

The factors governing the differential accumulation of Blec RNA in the epidermis probably include both ontogenetic and positional elements. For example, since the protodermis forms the outer layer of the apical meristem, the reduced levels of Blec within the protodermis may correspond to a zone of influence for diffusible factors defining the apical meristem. Alternatively, the transition from protodermal to epidermal cells could define a developmental progression within a single tissue layer. Thus, it is possible that only those cells sufficiently developed, and therefore of sufficient distance from the apical meristem are capable of expressing Blec. Further elucidation of the factors involved in regulating Blec expression should prove valuable with regard to an understanding of the processes involved in cell type differentiation within the shoot apex.

The exact position at which Blec transcripts first accumulate appears to be related to the polarity of the expressing leaf surface: this is particularly obvious when primordia are about 200–300 µm in length. At this stage, transcripts are undetectable in the adaxial surface of leaf primordia whilst accumulating to significant levels on the abaxial surface. This feature is depicted in FIG. 1A.

Figure 2A:
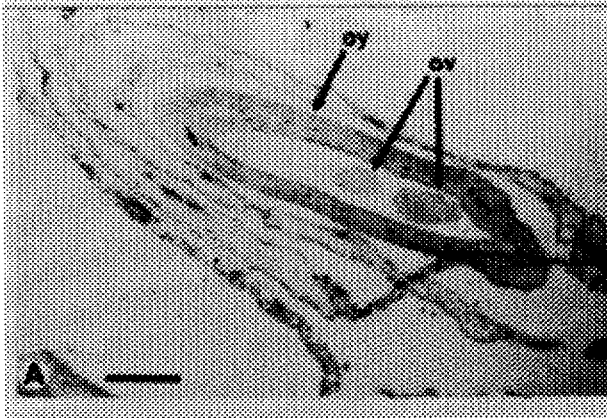
FIGS. 2A–D displays in situ hybridizations of longitudinal section through a developing pea ovary 1–2 days post fertilization. Blec RNA mainly accumulates in the outer epidermis, and is preferentially expressed on the epidermis of the developing ovule. oy, ovary; ov, ovule.
Figure 2B:
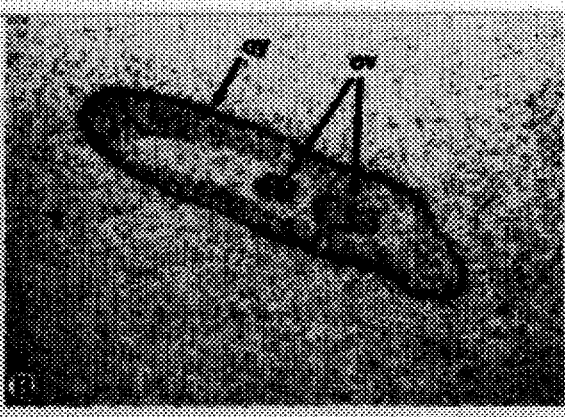

In floral apices, similar positional and stage specific expression within the epidermis are seen. Thus, in floral domes (FIG. 1B) and developing floral buds (FIG. 1C), Blec is undetectable in protodermal cells. As with vegetative primordia, Blec accumulates mainly on the outer or abaxial surface of floral organs. For example, in developing sepals, Blec is seen to accumulate specifically in the outer epidermis, equivalent to the abaxial surface of vegetative leaf (FIG. 1C). A particularly convincing example is seen in developing ovaries, immediately post pollination (FIGS. 1D and 2B). FIG. 2A shows a longitudinal section through an ovary several days after pollination. FIG. 2B shows an autoradiogram of the section shown in FIG. 2A which reveals that Blec RNA accumulates mainly in the outer epidermis of the ovary, and is present at significantly lower levels in the inner epidermis of the ovary. The unilocular ovary of Pisum sativum can be regarded as a folded leaf, the outer epidermis corresponds to the abaxial leaf surface, and the inner surface corresponds to the adaxial surface. It therefore seems that Blec accumulates in response to a in-built organ polarity not only in structures with an obvious lamina morphology, such as leaves and sepals, but also in non-lamina-like organs such as ovaries. The axis of polarity being defined by a line drawn between the two surfaces of the organ, rather than by proximity to a given meristem or external tropic influences. The nature of this polarity is unknown but may represent either hormonal or mechanical gradients across the organ.

Within the ovary Blec also accumulates in developing ovules (ov in FIG. 2B). Each ovule is little more than 30–50 µM in diameter, see FIG. 2B. While it is difficult to determine whether or not Blec is expressed preferentially in ovule epidermal cells, the lack of detectable levels of Blec RNA at later stages of ovule and seed development (17–30 days after flowering) as measured by Northern analysis, according to the methods of M. S. Dobres and W. F. Thompson, supra, appear to reflect both the mature state of such organs and the possible dilution of Blec RNA by other RNAs at that stage of development.

Figure 2C:
Figure 2D:
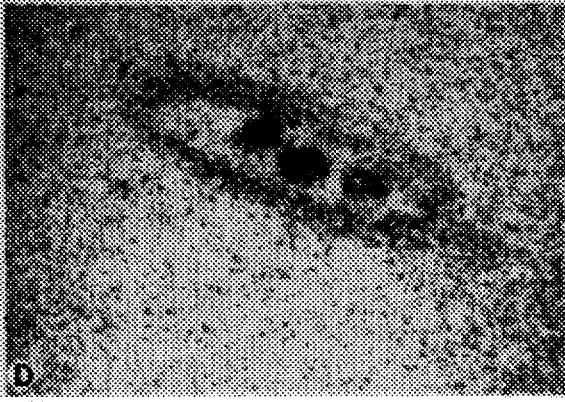

As a comparative control FIG. 2D shows an autoradiogram of FIG. 2C after hybridization with an antisense histone H1 RNA, prepared according to the methods of S. Gantt and J. L. Key, *Eur. J. Biochem.* 1987, 166, 119–125, incorporated herein by reference in its entirety, which reveals high levels of histone H1 RNA in the developing ovules and lower levels throughout the ovary.

Construction of Recombinant Blec4 Promoter-GUS Construct

Figure 6:
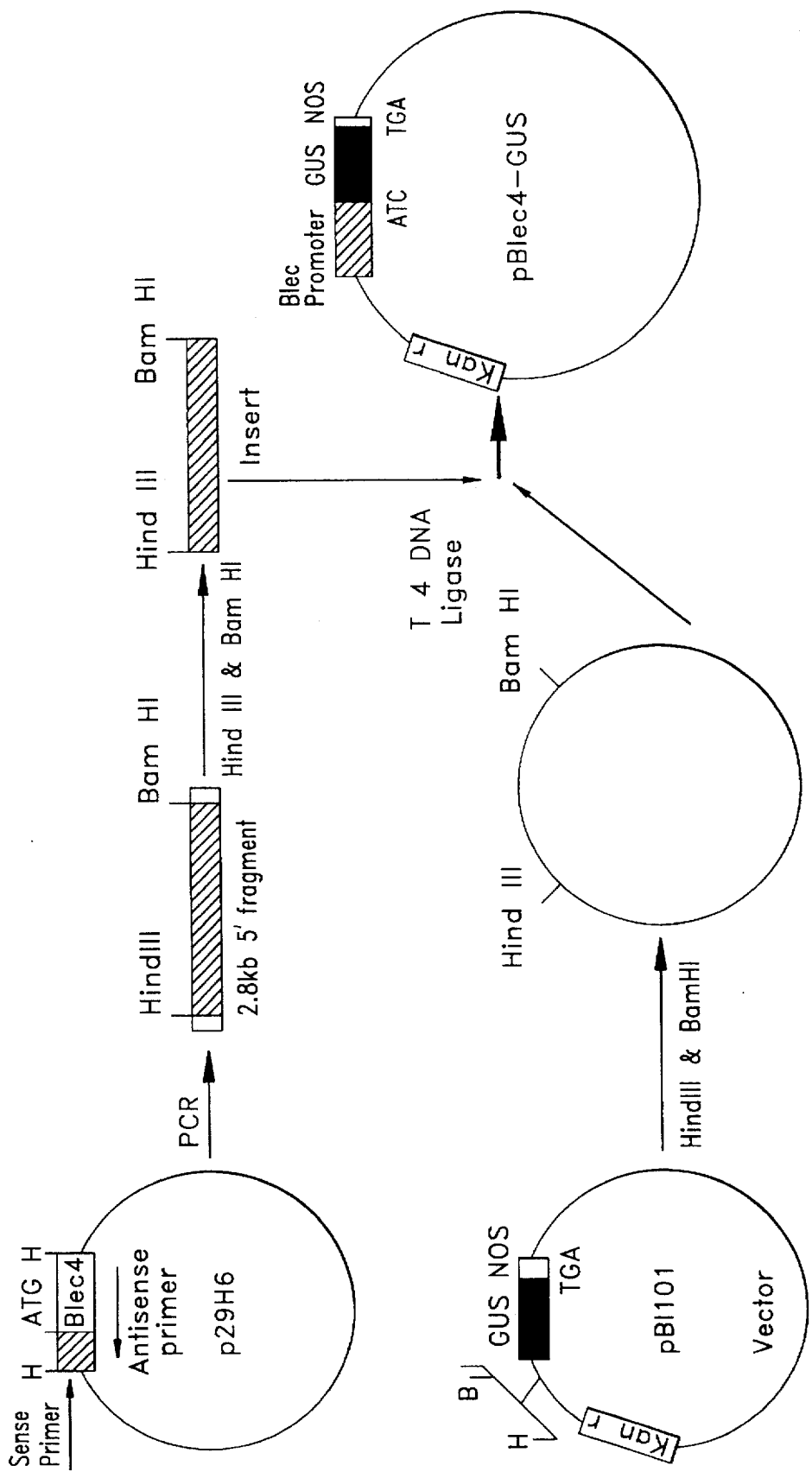
FIG. 6 displays the construction of pBlec4-GUS. The 2.8 kb promoter fragment was ligated into the HindIII-BamHI site of pB101 to produce pBlec4-GUS.

To determine if the 5' upstream sequences were capable of directing expression of foreign proteins in plants the following construct was made: a 2.8 kb fragment corresponding to the 5' upstream sequences of the Blec4 gene were subcloned from p29H6 by polymerase amplification according to the methods disclosed in *PCR Protocols, A Guide to Methods and Applications*, Eds., Innis, M. A., et al., Academic Press, San Diego, Calif., 1990, incorporated herein by reference in its entirety, using Taq polymerase and two nucleotide primers, 5' AATACGACTCACTATAG 3' and 5' CCGCGGATCCTCTAACTATTCTGAGATTTTG 3', set forth in SEQUENCE ID NOS: 3 and 4, respectively. The fragment was digested with HindIII and BamHI and ligated into the plant binary vector pB101 (Jefferson et al., supra) digested with HindIII and BamHI to create the vector pBlec4-GUS. The cloning strategy is depicted in FIG. 6.

Demonstration that the Blec4 Promoter can Direct Epidermal Specific Expression of a Bacterial Protein in Transgenic Plants The construct pBlec4-GUS was used to transform alfalfa RegenSY using the transformation process described above. Histochemical localization of pBlec4-GUS activity in transgenic alfalfa reveals that the Blec4 promoter directs expression of β-glucuronidase, a foreign protein, to the epidermis of transgenic alfalfa. Histochemical localization was performed as follows. Plant material was fixed in 90% acetone for 1 hour, at room temperature and washed with 50 mM Sodium Phosphate pH 7 for 2 hours. Plant material was then sectioned on a vibrotome to a thickness of 50 µM. Sections were then incubated in 100 mM sodium phosphate, 10 mM EDTA, 0.5 mM potassium ferricyanide, 0.5 mM potassium ferrocyanide and 1 mM 5-bromo-4-chloro-3-indolyl β-D-glucuronide for 3 hours and fixed in a solution containing 5% formaldehyde, 5% acetic acid and 20% ethanol for 10 minutes, washed with 50% ethanol for 2 minutes and finally washed with 95% ethanol before placing on slides and mounting with 80% glycerol. Sections were viewed with X10 and X40 objectives on a Nikon Photomat microscope and photographed using Ektachrome T160 film.

Figures 7A, 7B, 7C:
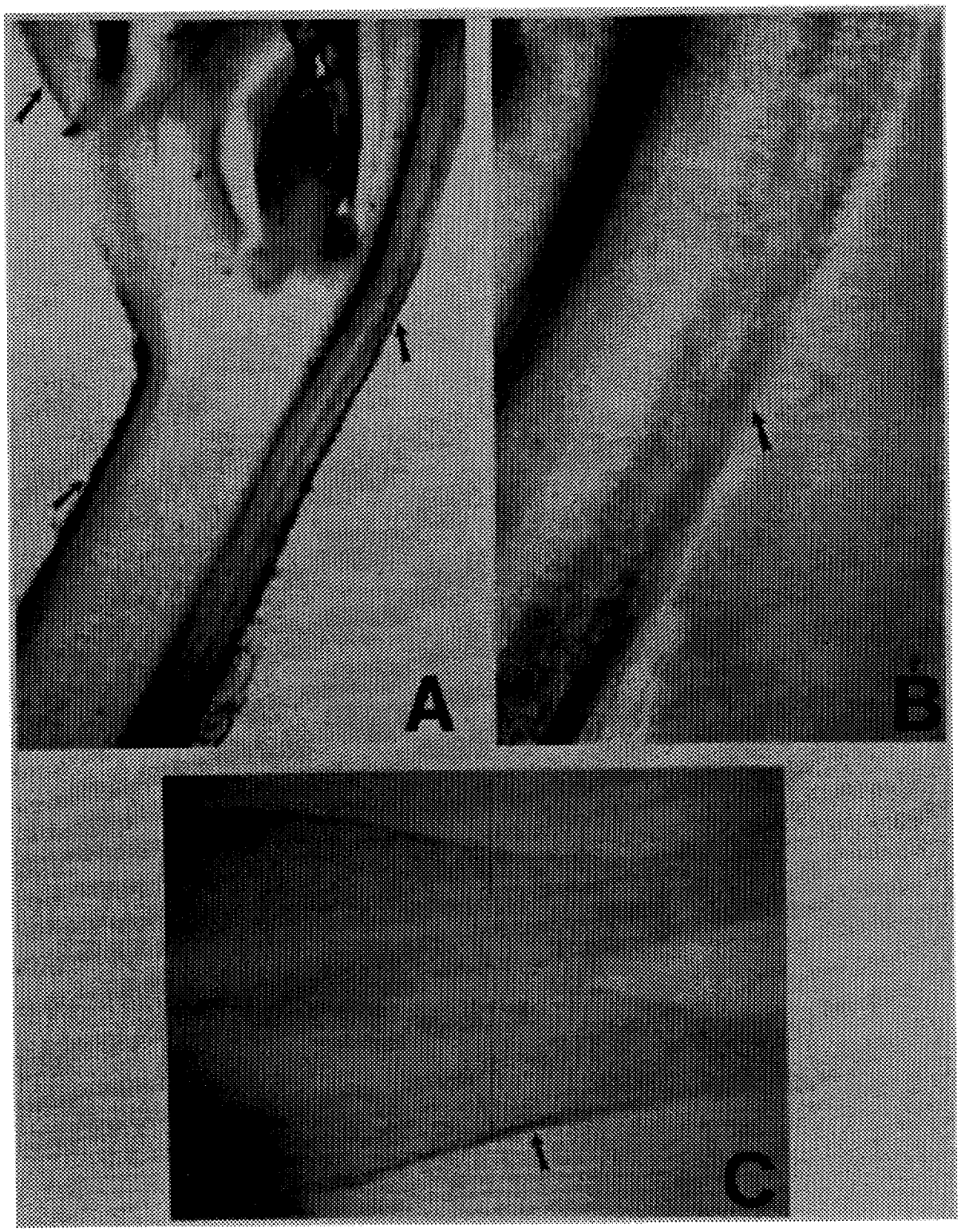
FIGS. 7A–C reveals the histochemical localization of pBLec4-GUS activity to the epidermis of transgenic alfalfa. Blue staining is due to conversion of a colorless XGluc substrate to a blue indole precipitate by Gus (β-Glucuronidase).

As shown in FIGS. 7A and B, staining was seen preferentially in the epidermis of transgenic alfalfa. Expression levels at several different developmental stages were examined. Staining was observed in somatic embryos, FIG. 7C, which demonstrates the utility of the Blec4 promoter for targeting foreign proteins to developing seeds during zygotic embryo development.

Preferential activity was also observed in the shoot tips of young plantlets and adult plants which demonstrates the utility of the Blec4 promoter for targeting foreign genes to the shoot tips of growing plants. Using this histochemical method, no β-glucuronidase activity was detected in expanded leaves or mature seem material.

Demonstration that the Blec4 Promoter Directs High Level Expression to the Shoot Apex To quantify the expression of the Blec4 promoter-GUS construct in transgenic alfalfa, use was made of the substrate 4-methylumbelliferyl-B-D-glucuronide (MUG). GUS hydrolyzes MUG to a fluorescent derivate 4-methylumbelliferone (MU). In this way, the activity of the Blec4 promoter-GUS construct can be quantified fluorometrically.

Quantification

Figure 8:
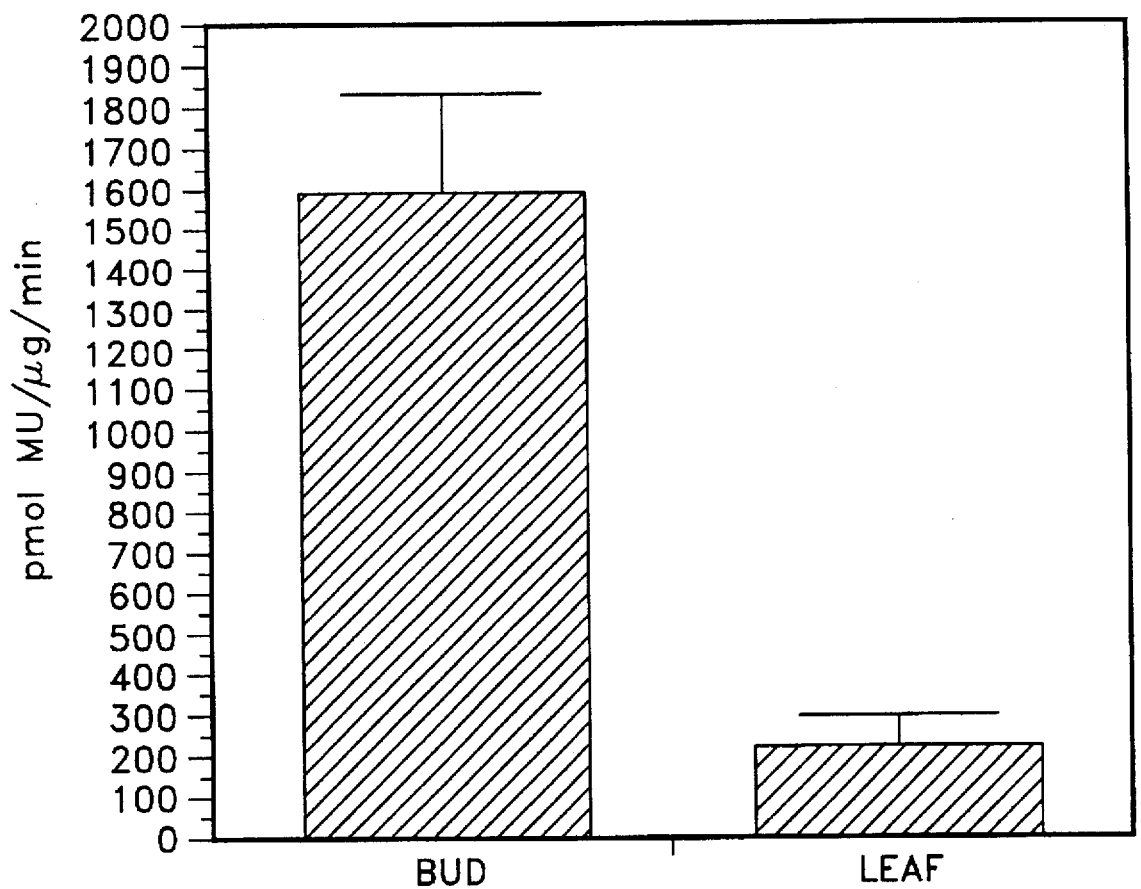
FIG. 8 shows the result of Blec4 promoter activity assays performed on protein extracts of buds and leaves (taken from the fifth node below the apical bud) of transgenic alfalfa. The values shown are the mean of three independent assays performed on each tissue type.

GUS activity assay: For fluorometric assays approximately 100 mg of plant tissue was ground in the presence of sterile glass beads with 100 µl of GUS extraction buffer (500 nM NHPO$_4$, pH 7.0, 10 mM B-mercaptoethanol, 10 mM Na$_2$EDTA, 0.1% Sarkosyl, 0.1% Triton X-100) and centrifuged at 10,000 r.p.m. in a microfuge for 10 minutes. The supernatant was removed to a fresh tube. Supernatants were stored at −80° C. Reactions were performed in a total volume of 200 µl GUS extraction buffer containing 20 µg of total protein extract, 20% methanol, 1 mM 4-methylumbelliferyl-B-D-glucuronide (MUG) at 37° C. for 2 hours. Reactions were stopped with 800 µl of 0.2M Na$_2$CO$_3$. MU fluorescence was determined at an excitation wavelength of 355 nm and an emission wavelength of 455 nm. Fluorescence readings were converted to pmoles MU by measuring the fluorescence of series of MU standards of known concentration. FIG. 8 shows the result of assays performed on protein extracts of buds and leaves (taken from the fifth node below the apical bud) of transgenic alfalfa. The values shown are the mean of three independent assays performed on each tissue type. It can be seen that the Blec4 promoter is expressed at approximately eight fold higher levels in the apical bud of transgenic alfalfa than in mature expanded leaves five nodes below the shoot apex.

Homology to Seed Lectins

The pea seed lectin (PSL) is highly expressed during seed development, Higgins, T. J. V., et al., *J. Biol. Chem.* 1983, 258, 9544–9549. Given the homology between Blec and PSL it was important to establish not only the relative expression patterns of both genes, but also whether Blec and PSL probes were specific for their respective transcripts. To do this, Northern blots of RNA samples from shoot apices and developing seeds were separately probed with Blec and PSL cDNAs according to the methods of M. S. Dobres and W. F. Thompson. The results clearly showed that as determined by Northern analysis (a) Blec does not accumulate to detectable levels in developing seeds, and (b) seed lectin transcripts do not accumulate to detectable seed levels in the shoot apex. Furthermore, neither probe cross-hybridized with transcripts of the other gene. The results also have been confirmed at the level of in situ hybridization, any detectable signal when hybridized against thin sections of the pea shoot apex.

The expression pattern of Blec suggests that it is responding to subtle developmental cues involved in specific developmental events during tissue and organ development. The Blec genes will prove useful as indispensable tools with which to understand the regulatory processes that occur during the development of the plant epidermis.

Based on the above described homology to PSL it was predicted that antibodies produced against the PSL would recognize Blec proteins. Furthermore, based on the above described homology, it was predicted the Blec protein present in plants would bind sugars and other carbohydrates. This prediction was used as a basis for the following purification protocol.

Purification of Blec from Pea Shoot Apices

Figure 9:
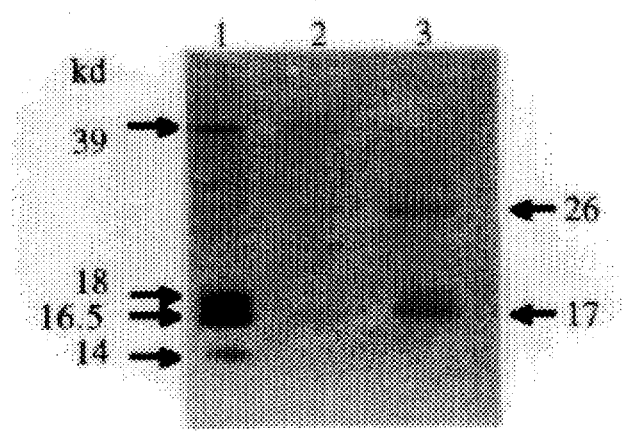
FIG. 9 is a gel showing the cross reaction of a 39 kd protein in pea shoot apices with pea seed lectin antisera. Lane 1: pea shoot apex; lane 2: expanded leaves, lane 3: seed.

To detect vegetative homologues of the pea seed lectin, anti-pea seed lectin was used to probe extracts from apical buds, expanded leaves, and seeds. Extracts were separated by SDS-PAGE electrophoresis and immobilized on nitrocellulose. A 1:500 dilution of pea seed lectin antisera, obtained from T. J. Higgins, CSIRO, Canberra, Australia, was reacted with the membrane. Cross-reacting proteins were visualized using alkaline-phosphatase conjugated secondary antibody. FIG. 9 shows the membrane after color development. The bud extract in lane 1 reveals a 39 kd band and several lower molecular weight bands of 14–18 kd. The 39 kd band appears to represent a glycosylated form of Blec (25 kd plus 2–3 glycosylation sites). The 14–18 kd bands appear to represent degradation products of the full length protein (the 14–18 kd bands are not seen when the protein is purified over a fetuin column, and therefore not thought to form part of an intact or correctly folded Blec molecule. The expanded leaf extract revealed a weaker signal for 39 kd band, see FIG. 9, lane 2. In FIG. 9, lane 3, the seed extract revealed a 26 kd band (seed-lectin precursor) and a 17 kd band (beta subunit of the pea seed lectin). The seed lectin is synthesized as a single polypeptide that is processed into beta and alpha subunits of 17 kd and 6 kd respectively (Higgins et al., 1983). The 6 kd subunit does not cross react with the pea seed lectin antisera because the antisera was made against native pea seed lectin in which the 6 kd sequences are internalized. The epitopes recognized by the seed lectin antibody in bud extracts probably represent the conserved beta-strand forming regions of Blec.

Figure 10:
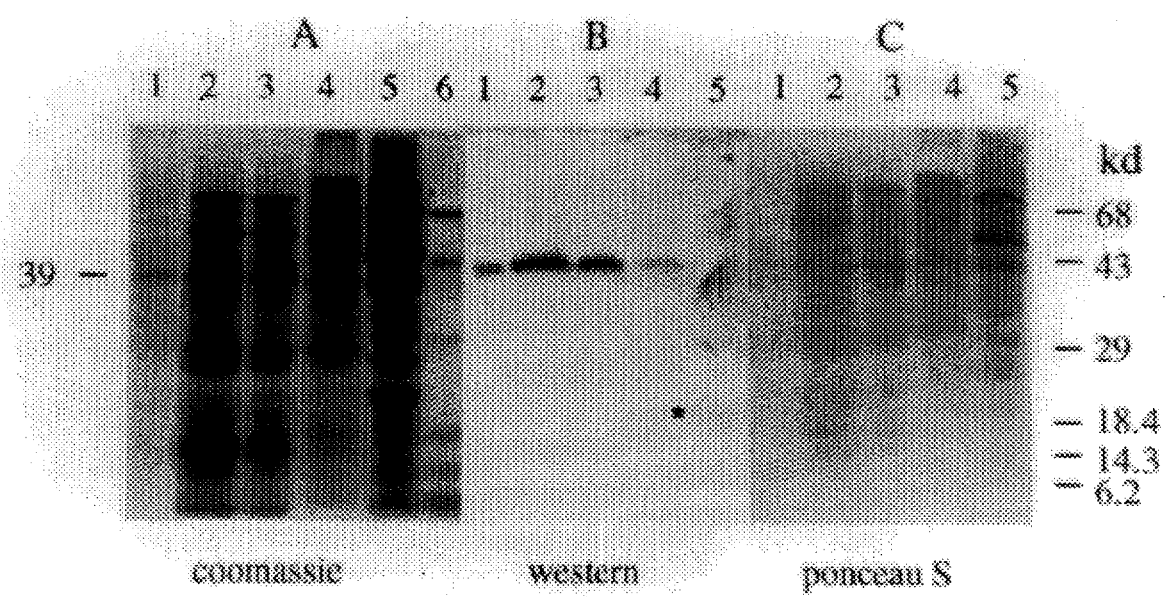
FIGS. 10A–C displays the purification of Blec by fetuin affinity chromatography.

To purify and verify the identity of the 39 kd protein, pea shoot apex extracts were purified by fetuin affinity chromatography. Fetuin was chosen because it is a glycoprotein bearing a broad range of N-linked and O-linked glycans, and thus acts as a broad range affinity column for lectins. A 30–80% ammonium sulfate fraction was loaded onto a 5 ml fetuin column, the column was washed with several column volumes of 10 mM phosphate 10 mM sodium chloride until the absorbance of the flow-through was close to zero. Bound protein was then eluted using 150 mM NaCl. The eluted proteins were analyzed by SDS-page electrophoresis, FIG. 10A. FIG. 10A, lane 1 shows that the 150 mM eluate fraction contains a prominent band of ca. 39 kd. A Western blot of an identical gel was probed with anti-pea seed lectin antisera. The pea seed lectin antisera reacted strongly against a 39 kd protein in the total extract, the 30–80% AS fraction, the 10 mM NaCl flow through, and the 150 mM eluate. The reduced signal of the 39 kd band in FIG. 9, lane 1 is due to inadvertent underloading of this lane, as evidenced by the ponceau S stain of the blot prior to antibody probing, FIG. 10C, lane 1. Higher salt washes (0.5M NaCl, and the addition of glucose, galactose, or EDTA) failed to elute any further detectable proteins from the fetuin column.

To determine the identity of fetuin purified protein from total extracts (10 µg) was subjected to N-terminal sequence analysis by the Protein Chemistry Laboratory at the University of Pennsylvania. FIG. 11 shows that the N-terminal sequence (39 kd in FIG. 11) matches the predicted N-terminus derived from the Blec cDNA sequence. The N terminus of legume lectins represents a highly variable region, and can be used to distinguish between Blec and the pea seed lectin (PEA), and all other lectins sequenced to date. The above protein data indicate that Blec (as represented by the 39 kd protein) accumulates as an apex specific protein, and that, as judged by its ability to bind to fetuin-agarose columns, is able to bind to glycoconjugates, however it is also possible that the binding of Blec to the fetuin column may have been mediated by other chemical or physical interactions such as ionic or hydrophobic interactions.

The sugar dependency of the 39 kd protein to fetuin was investigated and an elution of the 39 kd protein from the fetuin column was unsuccessful with 0.2M galactose dissolved in 10 mM phosphate and 10 mM NaCl. Separate elutions using glucose, galactose, arabinose, and rhamnose, each at 0.2M dissolved in 10 mM phosphate and 10 mM NaCl, were also unsuccessful. The inability of these monosaccharides and dissaccharides to elute Blec from the column may indicate that Blec binds oligosaccharides or complex sugars such as those present on plant glycoproteins or the polysaccharides of cell walls, and that Blec has a lower affinity for monosaccharides, and/or that the binding of Blec to fetuin may be mediated via hydrophobic interactions between fetuin and conserved hydrophobic pocket of Blec. In either case, Blec is selectively retained on a fetuin-agarose column. This interaction may reflect the ability of Blec to bind to glycoproteins and/or polysaccharide components of the plant cell.

Overexpression of a GST-Blec Fusion Protein in *E. coli*

Figure 12:
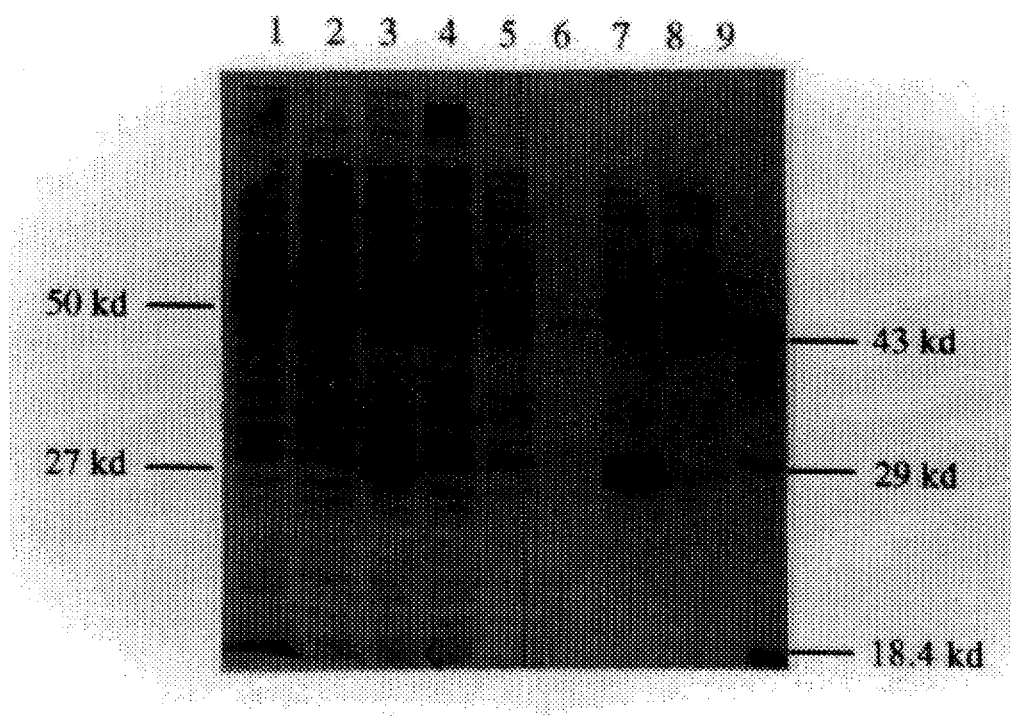
FIG. 12 reveals the results of a gel showing expression of GST-Blec fusion. Lanes: 1, induced pellet fraction of GST-Blec (50 kd); 2, uninduced GST-Blec soluble fraction; 3, induced GST pellet (27 kd); 4, uninduced GST pellet; 5, GST-Blec induced soluble fraction; 6, GST-Blec uninduced soluble fraction; 7, induced GST soluble fraction; 8, GST uninduced soluble fraction; and 9, molecular weight markers.

In the long term, structure-function studies of Blec require an abundant source of recombinant protein, and a defined set of Blec specific antibodies. Blec has been successfully expressed in *E. coli* as a GST-fusion protein. A DNA fragment corresponding to the predicted mature Blec protein was amplified by polymerase chain reaction from the Blec1 cDNA using Pfu polymerase. The primers were designed such that the fragment could be cloned in frame into the BamHI and EcoRI cloning sites of pGEX2T (Pharmacia). The cloning site lies downstream of taq promoter, a partial Glutathione S-Transferase sequence, and a thrombin cleavage site. The tag promoter allows IPTG induction of expression of the GST sequences ligated in frame to it. The GST sequence allows purification of the fusion protein over a glutathione-sepharose column. The thrombin cleavage site allows removal of the GST sequences from Blec. This system has been used to express antigen for antibody production. FIG. 12 shows a comparison between induced and uninduced cultures of the pellet and soluble fractions of *E. coli* lysates. The GST-Blec1 fusion protein is highly expressed in induced cultures and accumulates mainly in the pellet fraction as a 50 kd protein (27 kd of GST and 25 kd of Blec, see FIG. 12, lane 1). The GST-Blec1 fusion protein may be purified using glutathione-sepharose and is useful as an antigen for the production of Blec antisera. The protein may also be useful as a fungicidal, bacteriocidal, insecticidal, and/or antimicrobial for plants; or as means with which to purify or identify certain human, animal, fungal, or plant cell types.

Various modifications of the invention in addition to those shown and described herein will be apparent to those skilled in the art from the foregoing description. Such modifications are also intended to fall within the scope of the appended claims.

---

What is claimed is:

1. A method of transforming plants comprising:
   a. providing a plant,
   b. preparing a construct of a Blec promoter sequence of SEQ ID NO: 1 or a fragment thereof having epidermal specific activity and a heterologous gene, thereby producing a promoter-gene construct, and
   c. transforming said plant with said promoter-gene construct thereby producing a transformed plant.

2. The method of claim 1 wherein said plant is transformed in culture.

3. The method of claim 1 wherein said plant is from the family selected from the group consisting of Rosaceae, Euphorbiaceai, Caryophyllaceae, Solanaceae, Gesneriaceae, Balsaminaceae, Orchidaceae, Compositae, Geraniaceae, Lilaceae, Moraceae, Araceae, Leguminosae, Gramineae, and Umbelliferae.

4. A method of transcribing nucleic acids in vitro comprising
   a. preparing a cell-free extract derived from a plant,
   b. preparing a construct comprising a Blec promoter sequence of SEQ ID NO: 1 or a fragment thereof having epidermal specific activity and a heterologous gene under control of said promoter, and
   c. combining the extract of a. with the construct of b. under conditions suitable for in vitro transcription.

\* \* \* \* \*

UNITED STATES PATENT AND TRADEMARK OFFICE
CERTIFICATE OF CORRECTION

PATENT NO. : 5,744,334

DATED : Apr. 28, 1998

INVENTOR(S) : Dobres et al.

It is certified that error appears in the above-identified patent and that said Letters Patent is hereby corrected as shown below:

On the cover page, under "OTHER PUBLICATIONS", first column, at "Pak", please delete "Regualted" and insert --Regulated-- therefor.

On the cover page, under "OTHER PUBLICATIONS", first column, at "Maiti", second line thereof, please delete "teh" and insert --the-- therefor.

On the cover page, under "OTHER PUBLICATIONS", second column, at "Bogusz", third line thereof, please delete "*Plants Cell*" and insert --*Plant Cell*-- therefor.

On page 2, under "OTHER PUBLICATIONS", first column, at "W.F. Thompson", please delete "leveles" and insert --levels-- therefor.

In column 1, line 7, following "1994", please insert --, now U.S. Patent No. 5,646,333.--

In column 5, line 52, please delete "identify" and insert --identifying-- therefor.

In column 6, line 34, please delete "maybe" and insert --may be-- therefor.

In column 7, line 67, please delete "riot" and insert --not-- therefor.

In column 8, line 40, please delete "Phaeophpyceae," and insert --Phaeophyceae-- therefor.

UNITED STATES PATENT AND TRADEMARK OFFICE
CERTIFICATE OF CORRECTION

PATENT NO. : 5,744,334

DATED : Apr. 28, 1998

INVENTOR(S) : Dobres et al.

It is certified that error appears in the above-identified patent and that said Letters Patent is hereby corrected as shown below:

In column 8, line 45, please delete "Euphorbiaceai" and insert --Euphorbiaceae-- therefor.

In column 9, line 34, following "reference" please insert --in--.

In column 9, line 38, please delete "CDNA" and insert --cDNA-- therefor.

In column 13, line 50, please delete "seem" and insert --stem-- therefor.

In column 23, line 59, claim 3, please delete "Euphorbiaceai," and insert --Euphorbiaceae-- therefor.

Signed and Sealed this

Fifteenth Day of June, 1999

Attest:

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2861 base pairs
        ( B ) TYPE: nucleic acid
        ( C ) STRANDEDNESS: double ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

| | | | | | | |
|---|---|---|---|---|---|---|
| TCAAGCTTAT | GTAAATTATA | ATTATCGCCA | TTGAATTTTC | ATATTTAAA | AATATTTAAT | 60 |
| AATTATTTCC | TTTGTTAACC | CTACCATAAA | TACATGAGAT | ACATTTTCT | AAATACGTGA | 120 |
| TACATTTTTC | TGGAATACCA | CAAGCAACGA | AAAAAATCAA | AACTTAATCT | CATAAATCAC | 180 |
| TATACTATTA | GATATACAAT | ATAATTTGT | ATATTTTTT | AATTTTATC | AATATTTAAA | 240 |
| GTAAATGATG | AAGAAGTGGA | CAAACCTGAT | TCCTTTTGGA | CCGAAGAGGA | AAACATAAAA | 300 |
| TATGAAATTT | ATTTCAAAAC | CAATAGAATT | ATAACTATGT | CTCTAGATGA | TAGCAAATTT | 360 |
| TATTATGTTT | ATCGTTGTAA | AATCTTCAAG | GATATGTGGG | ATACTTTGA | AATAATATAT | 420 |
| GGAGATCTTC | CATATATCAA | GCAAGAGGAG | ATAAACATGA | AACAAGAAG | ATAAGGAGT | 480 |
| TCTAATAAGC | ATGTCTTGGT | GACTCCTAAT | CTATAATATG | ATAATATTGA | ATACTCTAAA | 540 |
| TCTATATGCT | TTAATTCAAT | GACAATATTA | TTAATAAATA | ATTGTTTTA | GATGTTAATA | 600 |
| TAACATCACT | CTTTATAAAA | ATTTGTTATA | GATATTAAAA | AAAAAATTAT | GCCAAATATT | 660 |
| TTTAAAGAT | CAGACTAAGA | AGAAAAAAAC | ATTAATGTGA | TATTTATTAA | CATTTATTTG | 720 |
| TTTAAAATAA | ATGATTAAST | TTTTATAAAA | AAATTAATCT | AAAAAATGAT | ATAAATTAAT | 780 |
| ATTTTAATAT | TGATTTAATA | CTGGCATATC | ACCATTATTA | CTAACATGTC | ATTAAAAATA | 840 |
| AGATTTAAAA | AAGTAATCTA | AAAAGAATAT | AAATTAATAT | TTAATATCG | ACTCGAATTA | 900 |
| GTAGTTAGTT | GGACACATTG | AATACTAGCT | TTTATGGCAC | TCCAATTAGT | TTGACACATT | 960 |
| GAATACTAGC | TTTCATTTCC | AAACCAAATT | TGTATCATTT | CCAAACCAAA | CTTGTTTCTT | 1020 |
| TTATAATAAT | TTCTGACATA | TGATAATACT | CCCTATCATT | TTTTATTATG | GTTGTTTTGA | 1080 |
| AAAAAAATTA | TATCATAATA | TAAATCATTT | TACAATGTTA | AAAAGAATTA | ATATTAGTTT | 1140 |
| TTTATTATAA | CTCTAGAATT | TTATTATTAT | CTTTTTTTTT | AATTATATAA | ATTTATCTTC | 1200 |
| TCCATTTTAT | TAATATATAA | AGATATTTTT | TTGATATAAT | TTTTTAATA | CGTGTAAAAA | 1260 |
| TCTAAAATAT | TAACTCCCTC | CGTTCTTTTT | TAAGTGTCAT | TTTTTTGATT | TTTGCACATA | 1320 |
| TCAAGGAAGC | TAATCATTAT | TGTTATTTTT | CAAACAATAA | TTCTTCTTTT | ACTTATAATA | 1380 |
| CCCTTAATTA | TTTATTCATT | CACTTTACTT | TTTCTCTCTC | TCCAATCATT | ATCTAGAGAT | 1440 |
| AATTTTGACA | AAATTGCAAT | TAATATTACC | TTGGACTTTG | CAAGTGACAA | TTAAAANAAA | 1500 |
| ACAATTTTTT | TTTGCAAGAA | AGTGACACTT | ATAAAGGAAC | GGAGGGAGTG | CATGTGAAAA | 1560 |
| GTTAAAACA | ATTTATAATA | AAACATAAAC | AATAAAATAA | TATTATCATA | GTTNGACACA | 1620 |
| TACAATAATG | ATATAGTAAC | ATGAATCCTT | CCTCCTCGTG | TTACATGCGC | TTCCTTTCTT | 1680 |
| TTCCAAAATT | AATATTAACA | TGGTTTACCT | GTATGAAAAT | TTTAAAACGA | TTTATAATAA | 1740 |
| AAAAAATGGA | AGATAATATA | ATATAAACAT | AGTTTGACAC | ATACTATAAT | ATCATAATCA | 1800 |
| TATAATTGCC | ACCTTAATGA | GTTGTGGACT | TGTATGTTCA | AAAAACACTG | TCTTCTATGT | 1860 |
| ATAAATTTAA | TACGTGTGAA | CAGTCTAAAA | CAATTTATAA | TAAAAAATAA | AGAATTATAT | 1920 |
| AATATTATCA | TAGTTGGACA | CAACAATAAT | ATCAGAATGA | TATAATGATA | TAGTAACATG | 1980 |
| TATGCTTCCT | CCTCGCGTTA | CATGTGCTTC | ATTTCTTTTA | CAAAATTATA | TTATTTAAAT | 2040 |
| AAATAAAATG | TGATTTTATT | TTCTTTTTAA | ATGTGTGAAA | TTATTATTAT | ATTCTATATA | 2100 |

```
TATATAAAAA  TATATTTAAA  TAGTGAAATA  GGGGCAAAAA  TATCCTTAAT  TATTTTTAAA    2160

AAAATTTAGA  TAAATAATGA  AAAACATATC  TAAAGAGAAA  AATAACCGAT  CATTTTTTTT    2220

AAATGTCAAA  TTTATTATTT  GTAAAGATTA  TTTTTAAATG  AAATGATAAG  ATAATGACAT    2280

ATAAGTGAGT  ATTTTATTTT  GTGAGGGGGA  CTTTTAAATA  ATTTTTTAAT  TATTTTTAAA    2340

CTAAAATACG  TAGTAACTAG  AAATCTATTC  CGTCTCGCCC  TGAACGTTTT  GATCGGCTTT    2400

GTTCTACTTT  TATATATTGA  TAAAAAAAAA  TTCGTAAAAG  AAAATTATCT  GGACGAGTCG    2460

CGTACTAGAT  CACTTTCTTT  AAGATATTTC  GTCATACTGT  CAATAATTAT  GCAATGCAGT    2520

CGGGTTTCGA  CGACATCTTC  AAGATAAAAC  AACCCATTCA  AAATTAGGTT  TTGATGAGTG    2580

ACACATTATA  ATTATTAATT  AATATTAATT  AATTAATTTT  CACCTAATTA  ACTTTCATTA    2640

ATTAATAGGG  ATGAGTTTTT  CAAATTCACA  TCAAGTATTC  CAGCAAAAGT  AAACTTTGGT    2700

GCATATAATA  TTTAACAGGT  GTTGTAAAAT  AATTTTAATG  ATATGTGATG  GTAAAAGTAC    2760

ACCCAAGTGC  CTATATAAAT  ATGTGTGATA  ACCAAATATA  TCCTCATTGA  TAACTTTGGT    2820

AACAAAATCT  CAGAATAGTT  AGAATGGCTT  TATATCGCAC  T                         2861

( 2 ) INFORMATION FOR SEQ ID NO:2:

( i ) SEQUENCE CHARACTERISTICS:
               ( A ) LENGTH: 3881 base pairs
               ( B ) TYPE: nucleic acid
               ( C ) STRANDEDNESS: double
               ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

TCAAGCTTAT  GTAAATTATA  ATTATCGCCA  TTGAATTTTC  ATATTTTAAA  AATATTTAAT      60

AATTATTTCC  TTTGTTAACC  CTACCATAAA  TACATGAGAT  ACATTTTTCT  AAATACGTGA     120

TACATTTTTC  TGGAATACCA  CAAGCAACGA  AAAAAATCAA  AACTTAATCT  CATAAATCAC     180

TATACTATTA  GATATACAAT  ATAATTTGT   ATATTTTTT   AATTTTATC   AATATTTAAA     240

GTAAATGATG  AAGAAGTGGA  CAAACCTGAT  TCCTTTGGA   CCGAAGAGGA  AAACATAAAA     300

TATGAAATTT  ATTTCAAAAC  CAATAGAATT  ATAACTATGT  CTCTAGATGA  TAGCAAATTT     360

TATTATGTTT  ATCGTTGTAA  AATCTTCAAG  GATATGTGGG  ATACTTTGA   AATAATATAT     420

GGAGATCTTC  CATATATCAA  GCAAGAGGAG  ATAAACATGA  AACAAGAAG   ATAAGGAGT      480

TCTAATAAGC  ATGTCTTGGT  GACTCCTAAT  CTATAATATG  ATAATATTGA  ATACTCTAAA     540

TCTATATGCT  TTAATTCAAT  GACAATATTA  TTAATAAATA  ATTGTTTTA   GATGTTAATA     600

TAACATCACT  CTTTATAAAA  ATTTGTTATA  GATATTAAAA  AAAAAATTAT  GCCAAATATT     660

TTTTAAAGAT  CAGACTAAGA  AGAAAAAAAC  ATTAATGTGA  TATTTATTAA  CATTTATTTG     720

TTTAAAATAA  ATGATTAAST  TTTTATAAAA  AAATTAATCT  AAAAAATGAT  ATAAATTAAT     780

ATTTTAATAT  TGATTTAATA  CTGGCATATC  ACCATTATTA  CTAACATGTC  ATTAAAAATA     840

AGATTTAAAA  AAGTAATCTA  AAAAGAATAT  AAATTAATAT  TTAATATCG   ACTCGAATTA     900

GTAGTTAGTT  GGACACATTG  AATACTAGCT  TTTATGGCAC  TCCAATTAGT  TTGACACATT     960

GAATACTAGC  TTTCATTTCC  AAACCAAATT  TGTATCATTT  CCAAACCAAA  CTTGTTTCTT    1020

TTATAATAAT  TTCTGACATA  TGATAATACT  CCCTATCATT  TTTTATTATG  GTTGTTTTGA    1080

AAAAAAATTA  TATCATAATA  TAAATCATTT  TACAATGTTA  AAAAGAATTA  ATATTAGTTT    1140
```

-continued

```
TTTATTATAA CTCTAGAATT TTATTATTAT CTTTTTTTTT AATTATATAA ATTTATCTTC    1200
TCCATTTTAT TAATATATAA AGATATTTTT TTGATATAAT TTTTTTAATA CGTGTAAAAA    1260
TCTAAAATAT TAACTCCCTC CGTTCTTTTT TAAGTGTCAT TTTTTTGATT TTTGCACATA    1320
TCAAGGAAGC TAATCATTAT TGTTATTTTT CAAACAATAA TTCTTCTTTT ACTTATAATA    1380
CCCTTAATTA TTTATTCATT CACTTTACTT TTTCTCTCTC TCCAATCATT ATCTAGAGAT    1440
AATTTTGACA AAATTGCAAT TAATATTACC TTGGACTTTG CAAGTGACAA TTAAAANAAA    1500
ACAATTTTTT TTTGCAAGAA AGTGACACTT ATAAAGGAAC GGAGGGAGTG CATGTGAAAA    1560
GTTAAAACA ATTTATAATA AAACATAAAC AATAAAATAA TATTATCATA GTTNGACACA    1620
TACAATAATG ATATAGTAAC ATGAATCCTT CCTCCTCGTG TTACATGCGC TTCCTTTCTT    1680
TTCCAAAATT AATATTAACA TGGTTTACCT GTATGAAAAT TTAAAACGA TTTATAATAA     1740
AAAAAATGGA AGATAATATA ATATAAACAT AGTTTGACAC ATACTATAAT ATCATAATCA    1800
TATAATTGCC ACCTTAATGA GTTGTGGACT TGTATGTTCA AAAAACACTG TCTTCTATGT    1860
ATAAATTTAA TACGTGTGAA CAGTCTAAAA CAATTTATAA TAAAAAATAA AGAATTATAT    1920
AATATTATCA TAGTTGGACA CAACAATAAT ATCAGAATGA TATAATGATA TAGTAACATG    1980
TATGCTTCCT CCTCGCGTTA CATGTGCTTC ATTTCTTTTA CAAAATTATA TTATTTAAAT    2040
AAATAAAATG TGATTTTATT TTCTTTTTAA ATGTGTGAAA TTATTATTAT ATTCTATATA    2100
TATATAAAAA TATATTTAAA TAGTGAAATA GGGGCAAAAA TATCCTTAAT TATTTTTAAA    2160
AAAATTTAGA TAAATAATGA AAAACATATC TAAAGAGAAA AATAACCGAT CATTTTTTTT    2220
AAATGTCAAA TTTATTATTT GTAAAGATTA TTTTTAAATG AAATGATAAG ATAATGACAT    2280
ATAAGTGAGT ATTTTATTTT GTGAGGGGGA CTTTTAAATA ATTTTTTAAT TATTTTTAAA    2340
CTAAAATACG TAGTAACTAG AAATCTATTC CGTCTCGCCC TGAACGTTTT GATCGGCTTT    2400
GTTCTACTTT TATATATTGA TAAAAAAAAA TTCGTAAAAG AAAATTATCT GGACGAGTCG    2460
CGTACTAGAT CACTTTCTTT AAGATATTTC GTCATACTGT CAATAATTAT GCAATGCAGT    2520
CGGGTTTCGA CGACATCTTC AAGATAAAAC AACCCATTCA AAATTAGGTT TTGATGAGTG    2580
ACACATTATA ATTATTAATT AATATTAATT AATTAATTTT CACCTAATTA ACTTTCATTA    2640
ATTAATAGGG ATGAGTTTTT CAAATTCACA TCAAGTATTC CAGCAAAAGT AAACTTTGGT    2700
GCATATAATA TTTAACAGGT GTTGTAAAAT AATTTTAATG ATATGTGATG GTAAAAGTAC    2760
ACCCAAGTGC CTATATAAAT ATGTGTGATA ACCAAATATA TCCTCATTGA TAACTTTGGT    2820
AACAAAATCT CAGAATAGTT AGAATGGCTT TATATCGCAC TAAAGAACTA GTCTCCCTTG    2880
TTTCAATCAT GTTTGTTTTG CTAGCCACAA ATATCGAAGC ACTTTCCTTC AATTTCCCCA    2940
AGATCACTCC TGGTAACACT GCTATCACCC TCCAAGGGAA TGCAAAGATT TTAGCCAATG    3000
GTGTCTTGGC ACTGACCAAC AGTACACAAA TTCCTCCAAC TACAACTTTC CCAAGTACAG    3060
GTCGTGCCTT ATATTCAACA CCCGTGCCTC TTTGGGACAG TGCTACCGGC AATGTTGCCA    3120
GTTTTGTCAC TTCCTTTTCT TTCGTCATAC TGAACCCGTC TGGACGTGTT CCAACTGATG    3180
GACTTGTATT TTTCATTGCA CCACCGGACA CTGAGATTCC CAACAACTCA CAAAGTCAAT    3240
ATCTGGGAGT AGTTGATAGT AAAACTTCAA TCAATCGATT CGTTGGTCTA GAGTTTGACC    3300
TTTATGCCAA TTCTTTCGAT CCCTATATGA GACATATTGG AATCGACATC AACTCTTTAA    3360
TTTCTACCAA GACCGTCAGA TATAACTTTG TGAGTGGTTC TTTGACTAAA GTAACTATAA    3420
TCTATGACTC TCCTTCTAAC ACCTTAACTG CTGTTATCAC TTATGAGAAT GGTCAAATTT    3480
CTACCATTTC ACAAAACGTT GATTGAAAG CTGTGCTCCC CAAGGACGTT AGCGTTGGTT    3540
```

```
TTTCTGCTAC  TTCAACAATT  GCCGTATCAC  ACAACATCCA  TTCATGGTCC  TTCACATCAA     3600

ACTTGGAAGC  AACTACTGGC  AATATCGTCT  CACAAGTATG  AATAATGCTT  ACTAGTTTCC     3660

TACTAGTTCT  AAATAAGACT  CTGCTTACTA  GCAGCTAATG  TAACCTCTAT  GTATGTGTTT     3720

TTCGATCATG  TTTCAATTAA  TGTTTCTTAC  TCTACATTCT  CCATTTTATT  TTTCTTAATT     3780

AGGCGAATAC  TTGTGTCATT  ACTAGCAAGG  TTCACACCCT  CACTCAACTC  GTGTCGTATG     3840

TTAATCGGTT  CATATACTTC  AATTACTCCT  CTTATAGTGA  A                          3881
```

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

```
AATACGACTC  ACTATAG                                                          17
```

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:4:

```
CCGCGGATCC  TCTAACTATT  CTGAGATTTT  G                                        31
```